United States Patent [19]

Sauerberg et al.

[11] Patent Number: 5,574,043
[45] Date of Patent: * Nov. 12, 1996

[54] CERTAIN [1,2,5-THIADIAZOL-4-YL]-1-AZABICYCLO [3.2.1]OCTANE DERIVATIVES AND THEIR PHARMACEUTICAL USES

[75] Inventors: Per Sauerberg, Farum; Preben Olesen, Copenhagen, both of Denmark

[73] Assignee: Novo Nordisk A/S, Bagsvaerd, Denmark

[*] Notice: The term of this patent shall not extend beyond the expiration date of Pat. No. 5,418,240.

[21] Appl. No.: 452,033

[22] Filed: May 26, 1995

Related U.S. Application Data

[60] Division of Ser. No. 204,832, Mar. 2, 1994, Pat. No. 5,527,813, which is a continuation-in-part of Ser. No. 26,943, Mar. 5, 1993, Pat. No. 5,418,240, which is a continuation-in-part of Ser. No. 744,160, Aug. 13, 1991, Pat. No. 5,260,314.

[51] Int. Cl.[6] .......................... C07D 451/02; A61K 31/46
[52] U.S. Cl. .......................... 514/304; 546/112; 546/125; 546/133; 546/137; 548/452
[58] Field of Search .............................. 546/125; 514/304

[56] References Cited

U.S. PATENT DOCUMENTS

| | | | |
|---|---|---|---|
| 5,041,455 | 8/1991 | Sauerberg et al. | 514/342 |
| 5,043,345 | 8/1991 | Sauerberg et al. | 514/342 |
| 5,418,240 | 5/1995 | Sauerberg et al. | 514/305 |

FOREIGN PATENT DOCUMENTS

| | | |
|---|---|---|
| 0239309 | 9/1987 | European Pat. Off. . |
| 0244018 | 11/1987 | European Pat. Off. . |
| 0296721 | 12/1988 | European Pat. Off. . |
| 0301729 | 2/1989 | European Pat. Off. . |
| 0307142 | 3/1989 | European Pat. Off. . |
| 0316718 | 5/1989 | European Pat. Off. . |
| 0322182 | 6/1989 | European Pat. Off. . |
| 0328200 | 8/1989 | European Pat. Off. . |
| 0349956 | 1/1990 | European Pat. Off. . |
| 0384285 | 8/1990 | European Pat. Off. . |
| 0459568 | 12/1991 | European Pat. Off. . |
| WO92/03433 | 3/1992 | WIPO . |

*Primary Examiner*—Alan L. Rotman
*Attorney, Agent, or Firm*—Steve T. Zelson, Esq.; Elias J. Lambiris, Esq.

[57] ABSTRACT

The present invention relates to therapeutically active azabicyclic compounds, a method of preparing the same and to pharmaceutical compositions comprising the compounds. The novel compounds are useful as stimulants of the cognitive function of the forebrain and hippocampus of mammals and especially in the treatment of Alzheimer's disease, severe painful conditions and glaucoma.

67 Claims, No Drawings

CERTAIN [1,2,5-THIADIAZOL-4-YL]-1-AZABICYCLO [3.2.1]OCTANE DERIVATIVES AND THEIR PHARMACEUTICAL USES

CROSS-REFERENCE TO RELATED APPLICATIONS

This is a divisional of Ser. No. 08/204,832 filed Mar. 2, 1994, U.S. Pat. No. 5,527,813 which is a continuation-in-part of Ser. No. 08/026,943 filed Mar. 5, 1993, U.S. Pat. No. 5,418,240 which is a continuation-in-part of Ser. No. 07/744,160 filed Aug. 13, 1991, U.S. Pat. No. 5,260,314.

BACKGROUND OF THE INVENTION

1. Field of the Invention

The present invention relates to therapeutically active azabicyclic compounds, a method of preparing the same and to pharmaceutical compositions comprising the compounds.

The novel compounds are useful as stimulants of the cognitive function of the forebrain and hippocampus of mammals and especially in the treatment of Alzheimer's disease.

2. Description of Related Art

Due to the in general improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. This disease is combined with, and also most likely caused by, a up to 90% degeneration of the muscarinic cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation and recognition.

It is a characteristic of Alzheimer's disease that although the cholinergic neurons degenerate, then the postsynaptic muscarinic receptors in the forebrain and hippocampus still exist. Therefore muscarinic cholinergic agonists are useful in the treatment of Alzheimer's disease and in improving the cognitive functions of elderly people.

It is well known that arecoline (methyl 1-methyl-1,2,5,6-tetrahydropyridine-3carboxylate) is such a cholinergic agonist.

Arecoline however has a very short biological half life and a small separation between central and peripheral muscarinic effects. Furthermore arecoline is a rather toxic compound.

EP-A-0307142 discloses a class of thiadiazoles, substituted on one of the ring carbon atoms with a non-aromatic azacyclic or azabicyclic ring system, and substituted on the other ring carbon atom with a substituent of low lipophilicity, or a hydrocarbon substituent, which are muscarinic agonists and therefore useful in the treatment of neurological and mental illnesses and severe painful conditions.

It is an object of the invention to provide new muscarinic cholinergic compounds.

SUMMARY OF THE INVENTION

The novel compounds of the invention are heterocyclic compounds having the formula I

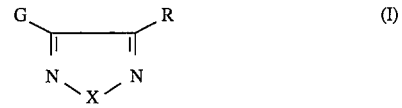

wherein

X is oxygen or sulphur;

R is hydrogen, amino, halogen, —CHO, —NO$_2$, —OR$^4$, —SR$^4$, —SOR$^4$, —SO$_2$R$^4$, C$_{3-7}$-cycloalkyl, C$_{4-8}$-(cycloalkylalkyl), —Z—C$_{3-7}$-cycloalkyl and —Z—C$_{4-8}$-(cycloalkylalkyl) wherein R$^4$ is straight or branched C$_{1-15}$-alkyl, straight or branched C$_{2-15}$-alkenyl, straight or branched C$_{2-15}$-alkynyl, each of which is optionally substituted with one or more halogens, —CF$_3$, —CN, —OH, phenyl or phenoxy wherein phenyl or phenoxy is optionally substituted with halogen, —CF$_3$, —CN, C$_{1-4}$-alkyl, C$_{1-4}$-alkoxy, —OCF$_3$, —CONH$_2$ or —CSNH$_2$; or R is phenyl or benzyloxycarbonyl, each of which is optionally substituted with halogen, —CN, C$_{1-4}$-alkyl, C$_{1-4}$-alkoxy, —OCF$_3$, —CONH$_2$ or —CSNH$_2$; or R is —OR$^5$Y, —SR$^5$Y, —OR$^5$ZY, —SR$^5$ZY, —O—R$^4$—Z—R$^5$ or —S—R$^4$—Z—R$^5$ wherein Z is oxygen or sulphur, R$^5$ is straight or branched C$_{1-15}$-alkyl, straight or branched C$_{2-15}$-alkenyl, straight or branched C$_{2-15}$-alkynyl, and Y is a 5 or 6 membered heterocyclic group containing one to four N, O or S atom(s) or a combination thereof, which heterocyclic group is optionally substituted at carbon or nitrogen atom(s) with straight or branched C$_{1-6}$-alkyl, phenyl or benzyl, or which heterocyclic group is optionally fused with a phenyl group; and G is selected from one of the following azabicyclic rings

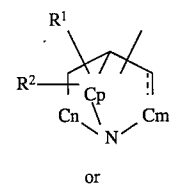

or

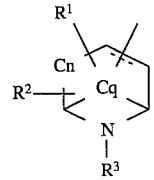

wherein the thiadiazole or oxadiazole ring can be attached at any carbon atom of the azabicyclic ring; R$^1$ and R$^2$ may be present at any position, including the point of attachment of the thiadiazole or oxadiazole ring, and independently are hydrogen, straight or branched C$_{1-5}$-alkyl, straight or branched C$_{1-10}$-alkoxy, straight or branched C$_{1-5}$-alkyl substituted with —OH, —OH, halogen, —NH$_2$ or carboxy; R$^3$ is H, straight or branched C$_{1-5}$-alkyl, straight or branched C$_{2-5}$-alkenyl or straight or branched C$_{2-5}$-alkynyl; n is 0, 1 or 2; m is 0, 1 or 2; p is 0, 1 or 2; q is 1 or 2; and

== is a single or double bond; or a pharmaceutically acceptable salt thereof.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically acceptable inorganic or organic acid addition salt.

The compounds of this invention are also useful analgesic agents and therefore useful in the treatment of severe painful conditions.

Furthermore, the compounds of this invention are useful in the treatment of glaucoma.

The invention also relates to methods of preparing the above mentioned compounds, comprising:

a) reacting a compound of formula II

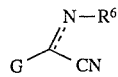
(II)

wherein G has the meaning defined above,

is

or

and $R^6$ is H, OH or O-alkyl, with $S_2Cl_2$ to form a compound of formula III

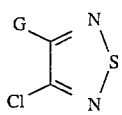
(III)

wherein G has the meaning defined above; subsequent displacement of Cl with an appropriate nucleophile gives a compound of formula I wherein X is S, or b) dehydrating a compound of formula IV

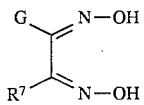
(IV)

wherein G has the meaning defined above and $R^7$ is alkyl, amino, halogen, alkoxy or alkylthio, to form a compound of formula V

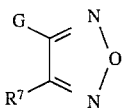
(V)

wherein G and $R^7$ have the meanings defined above, or c) when $R^7$ in formula V is amino, the amino group can be substituted by chloro by known procedures, and subsequent displacement of Cl with an appropriate nucleophile gives a compound of formula I wherein X is O, or d) oxidizing a compound of formula V

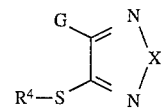
(VI)

wherein G, $R^4$ and X have the meanings defined above by standard procedures to form a compound of formula VII

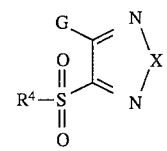
(VII)

and subsequent displacement of $-SO_2-R^4$ with an appropriate nucleophile to form a compound of formula I.

It is to be understood that the invention extends to each of the stereoisomeric forms of the compounds of formula I as well as the racemates.

The pharmacological properties of the compounds of the invention can be illustrated by determining their capability to inhibit the specific binding of $^3$H-Oxotremorine-M ($^3$H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

$^3$H-Oxo labels muscarinic receptor in the CNS (with a preference for agonist domains of the receptors). Three different sites are labelled by $^3$H-Oxo. These sites have affinity of 1.8, 20 and 3000 nM, respectively. Using the present experimental conditions only the high and medium affinity sites are determined.

The inhibitory effects of compounds on $^3$H-Oxo binding reflects the affinity for muscarinic acetylcholine receptors.

All preparations are performed at 0°–4° C. unless otherwise indicated. Fresh cortex (0.1–1 g) from male Wistar rats (150–250 g) is homogenized for 5–10 s in 10 ml 20 mM Hepes pH: 7.4, with an Ultra-Turrax homogenizer. The homogenizer, is rinsed with 10 ml of buffer and the combined suspension centrifuged for 15 min at 40,000×g. The pellet is washed three times with buffer. In each step the pellet is homogenized as before in 2×10 ml of buffer and centrifuged for 10 min at 40,000×g.

The final pellet is homogenized in 20 mM Hepes pH: 7.4 (100 ml per g of original tissue) and used for binding assay. Aliquots of 0.5 ml is added 25 μl of test solution and 25 μl of $^3$H-Oxotremorine (1.0 nM, final concentration) mixed and incubated for 30 min at 25° C. Non-specific binding is determined in triplicate using arecoline (1 μg/ml, final concentration) as the test substance. After incubation samples are added 5 ml of ice-cold buffer and poured directly onto Whatman GF/C glass fibre filters under suction and immediately washed 2 times with 5 ml of ice-cold buffer. The amount of radioactivity on the filters are determined by conventional liquid scintillation counting. Specific binding is total binding minus non specific binding.

Test substances are dissolved in 10 ml water (if necessary heated on a steam bath for less than 5 minutes) at a concentration of 2.2 mg/ml. 25–75% inhibition of specific binding must be obtained before calculation of $IC_{50}$.

The test value will be given as $IC_{50}$ (the concentration (ng/ml) of the test substance which inhibits the specific binding of $^3$H-Oxo by 50%).

IC$_{50}$=(applied test substance concentration)

$$x \frac{1}{\left(\frac{C_o}{C_x} - 1\right)} \text{ ng/ml}$$

where $C_o$ is specific binding in control assays and $C_x$ is the specific binding in the test assay. (The calculations assume normal mass-action kinetics).

Test results obtained by testing some compounds of the present invention will appear from the following table 1.

TABLE 1

| Compound No. | Inhibition in vitro OXO BINDING (ng/ml) |
|---|---|
| 1 | 156 |
| 2 | 270 |
| 3 | 208 |
| 4 | 21 |
| 5 | 18 |
| 6 | >300 |
| 7 | 13 |
| 8 | 5.2 |
| 9 | 0.69 |
| 10 | 1.7 |
| 11 | 1.2 |
| 12 | 0.45 |
| 13 | 0.65 |
| 14 | 4.8 |
| 15 | 0.61 |
| 16 | 67 |
| 17 | 3.2 |
| 18 | 7.5 |
| 20 | 11 |
| 21 | 0.96 |
| 22 | 3.4 |
| 23 | 43 |
| 24 | 0.52 |
| 25 | 1.9 |
| 26 | 1.4 |
| 27 | 17 |
| 28 | 1.9 |
| 29 | 0.39 |
| 30 | 0.13 |
| 31 | 0.6 |
| 32 | 0.45 |
| 33 | 6.4 |
| 34 | 7.9 |
| 35 | 1.9 |
| 36 | 0.82 |
| 37 | 2.0 |
| 39 | 0.52 |
| 40 | 0.19 |
| 41 | 0.56 |
| 42 | 0.35 |
| 43 | 2.33 |
| 44 | 4.7 |
| 45 | 1.6 |
| 46 | 0.56 |
| 47 | >300 |
| 48 | 0.43 |
| 49 | 0.33 |
| 50 | 1.0 |
| 51 | 0.89 |
| 52 | 0.61 |
| 53 | 0.3 |
| 54 | 3.1 |
| 55 | 0.43 |
| 56 | 0.14 |
| 57 | 4.6 |
| 62 | 1.9 |
| 63 | 8.2 |
| 64 | 8.2 |
| 65 | 9.6 |
| 67 | 0.43 |
| 68 | 0.69 |
| 74 | 0.45 |
| 75 | 0.96 |
| 76 | 2.6 |
| 77 | 0.89 |
| 78 | 0.30 |
| 79 | 0.50 |
| 80 | 0.30 |
| 81 | 0.40 |
| 82 | 0.40 |
| 83 | 0.43 |
| 84 | 13 |
| 85 | 7.2 |
| 86 | 3.5 |
| 87 | 10 |
| 88 | 6.1 |
| 89 | 12 |
| 90 | 3.3 |
| 91 | 5.2 |
| 92 | 1.5 |
| 93 | 9.0 |
| 94 | 12 |
| 95 | 1.7 |
| 96 | 0.3 |
| 98 | 1.0 |
| 100 | 0.82 |
| 101 | 0.75 |
| 102 | 1.52 |
| 103 | 0.92 |
| 104 | 0.85 |
| 106 | 0.9 |
| 107 | 0.3 |
| 108 | 16 |
| 109 | 4.0 |
| 110 | 1.1 |
| 111 | 0.32 |
| 112 | 0.19 |
| 113 | 0.26 |
| 114 | 0.15 |
| 115 | 0.50 |
| 116 | 1.4 |
| 117 | 2.0 |
| 118 | 0.35 |
| 119 | 0.30 |
| 120 | 0.28 |
| 121 | 0.32 |
| 122 | 0.67 |
| 123 | 0.47 |
| 130 | 0.60 |
| 131 | 0.96 |
| 132 | 0.96 |
| 133 | 0.45 |
| 134 | 0.47 |

The compounds of the invention, together with a conventional adjuvant, carrier, or diluent, and if desired in the form of a pharmaceutically acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective muscarinic cholinergic agonistic amount of the active ingredient commensurate with the intended daily dosage range to be employed. Tablets containing ten (10) milligrams of the active ingredient or, more broadly, one (1) to hundred (100) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethyl cellulose and polyvinylpyrrolidone.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil. Ampoules are convenient unit dosage forms. Tablets, dragees, or capsules having talc and/or a carbohydrate carrier or binder or the like, the carrier preferably being lactose and/or corn starch and/or potato starch, are particularly suitable for oral application. A syrup, elixir of the like can be used in cases where a sweetened vehicle can be employed.

Generally, the compounds of this invention are dispensed in unit form comprising 1–100 mg in a pharmaceutically acceptable carrier per unit dosage.

The dosage of the compounds according to this invention is 1–100 mg/day, preferably 10–70 mg/day, when administered to patients, e.g. humans, as a drug.

A typical tablet which may be prepared by conventional tabletting techniques contains:

| Active compound | 5.0 mg |
| Lactosum | 67.8 mg Ph.Eur. |
| Avicel ® | 31.4 mg |
| Amberlite ® | 1.0 mg |
| Magnesii stearas | 0.25 mg Ph.Eur. |

Due to the high muscarinic cholinergic receptor agonistic activity, the compounds of the invention are extremely useful in the treatment symptoms related to a reduction of the cognitive functions of the brain of mammals, when administered in an amount effective for stimulating the cognitive functions of the forebrain and hippocampus. The important stimulating activity of the compounds of the invention includes both activity against the pathophysiological disease, Alzheimer's disease as well as against normal degeneration of brain function. The compounds of the invention may accordingly be administered to a subject, e.g., a living animal body, including a human, in need of stimulation of the cognitive functions of the forebrain and hippocampus, and if desired in the form of a pharmaceutically acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically acceptable carrier or diluent, especially and preferably in the form of a pharmaceutical composition thereof, whether by oral, rectal, or parenteral (including subcutaneous) route, in an effective forebrain and hippocampus stimulating amount, and in any event an amount which is effective for improving the cognitive function of mammals due to their muscarinic cholinergic receptor agonist activity. Suitable dosage ranges are 1–100 milligrams daily, 10–100 milligrams daily, and especially 30–70 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1

A. Ethyl (1-azabicyclo[2.2.2]octan-3-ylidine)cyanoacetate

A solution of 3-quinuclidone (75 g, 0.6 mol), ammonium acetate (2.3 g, 30 mmol), acetic acid (3.75 ml) and ethyl cyanoacetate (67.8 g, 0.6 mol) in toluene (400 ml) was refluxed with a water separator for 18 h. Water (100 ml) and NaOH was added, and the mixture extracted several times with ether. The organic phases were dried and evaporated. The residue was purified by column chromatography (eluent: EtOAc/MeOH (2:1)), yielding 73 g of the title compound.

B. Ethyl (1-azabicyclo[2.2.2]octan-3-yl)cyanoacetate

A solution of ethyl (1-azabicyclo[2.2.2]octan-3-ylidene)cyanoacetate (73 g, 0.33 mol) in absolute ethanol (1 l) was treated with 10% palladium on charcoal (10 g) and hydrogen in a parr shaker at 20 psi for 5 h. Filtration and evaporation gave the wanted product in 68 g yield.

C. (1-Azabicyclo[2.2.2]octan-3-yl)hydroxyiminoacetonitrile

Ethyl (1-azabicyclo[2.2.2]octan-3-yl)cyanoacetate (10 g, 45 mmol) was added to a solution of sodium (1.04 g, 45 mmol) in absolute ethanol (60 ml). The mixture was stirred for 15 min. at room temperature and isoamylnitrite (7.9 ml, 60 mmol) was added. The reaction mixture was stirred for 18 h at 60° C. Evaporation of the reaction mixture gave crude title compound, which was used without further purification.

D. 3-Chloro-3-(3-chloro-1,2,5-thiadiazol-4-yl)-1-azabicyclo[2.2.2]-octane oxalate To a solution of crude (1-azabicyclo[2.2.2]octan-3-yl)hydroxyiminoacetonitrile (max. 45 mmol) in DMF (60 ml) was slowly added a solution of $S_2Cl_2$ (10.85 ml, 135 mmol) in DMF (20 ml) at 0° C. After addition the reaction mixture was stirred at room temperature for 48 h. Water and 50% NaOH was added to the ice cooled reaction mixture and extracted with ether. The combined ether phases were dried and evaporated. The residue was purified by column chromatography (eluent: EtOAc/MeOH (2:1)) to give the free base of the title compound in 1.04 g yield. Crystallization with oxalic acid from acetone gave an analytical pure product (Compound 1). M.p. 137°–139° C.

EXAMPLE 2

3-(3-Chloro-1,2,5-thiadiazol-4-yl)-3-
hydroxy-1-azabicyclo[2.2.2]octane oxalate

A solution of 3-chloro-3-(3-chloro-1,2,5-thiadiazol-4-yl)-1-azabicyclo[2.2.2]octane (250 mg, 0.95 mmol) in ethanol (25 ml) was treated with formic acid (750 μl, 20 mmol), triethylamine (4.2 ml, 30 mmol) and 10% palladium on charcoal for 18 h at 60° C. After filtration and evaporation water and $K_2CO_3$ was added to the residue and extracted with ether. The dried ether phases were evaporated and purified by column chromatography (eluent: EtOAc/MeOH (2:1)). Crystallization as the oxalate from acetone gave the title compound in 150 mg yield. (Compound 2). M.p. 241°–242° C.

EXAMPLE 3

3-Methoxy-3-(3-methoxy-1,2,5-thiadiazol-4-yl)-
1-azabicyclo[2.2.2]octane oxalate and
3-(3-Methoxy-1,2,5-thiadiazol-4-yl)-
1-azabicyclo[2.2.2]oct-2-ene oxalate A solution of 3-chloro-3-(3-chloro-1,2,5-thiadiazol-4-yl)-1-azabicyclo[2.2.2]octane (500 mg, 1.9 mmol) and sodiummethoxide (20 mmol) in methanol(20 ml) was stirred for 48 h at 60° C. Water was added to the reaction mixture and extracted with ether. The combined organic phases were dried and evaporated. The two products were separated by column chromatography (eluent: EtOAc/MeOH (2:1)). Crystallization of the dimethoxy product as the oxalate from acetone gave 200 mg. (Compound 3). M.p. 113°–117° C. The monomethoxy oxalate was isolated in 60 mg yield (Compound 4). M.p. 143°–145° C.

EXAMPLE 4

3-(3-Hexyloxy-1,2,5-thiadiazol-4-yl)-1-
azabicyclo[2.2.2]oct-2-ene oxalate,
3-Hexyloxy-3-(3-hexyloxy-1,2,5-thiadiazol-
4-yl)-1-azabicyclo[2.2.2]octane oxalate and
3-(3-Hexyloxy-1,2,5-thiadiazol-4-yl)-3-
hydroxy-1-azabicyclo[2.2.2]octane oxalate A 50% sodiumhydride dispersion (960 mg, 20 mmol) was dissolved in 1-hexanol and 3-chloro-3-(3-chloro-1,2,5-thiadiazol-4-yl)-1-azabicyclo[2.2.2]octane (500 mg, 1.9 mmol) was added. The reaction mixture was stirred at 90° C. for 18 h and evaporated. The residue was dissolved in water and extracted with ether. The dried ether phases were evaporated and the products separated by column chromatography (eluent: EtOAc/MeOH (2:1)). The first fractions contained the eliminated product which, after crystallization with oxalic acid, was collected in 70 mg yield. (Compound 5). M.p. 135°–137° C.

The next fractions contained the dihexyloxy analogue, which gave 70 mg as the oxalate salt. (Compound 6). M.p. 84°–85° C.

The later fractions gave the hydroxy-hexyloxy compound in 100 mg yield as the oxalate, salt. (Compound 7). M.p. 145°–147° C.

EXAMPLE 5

3-(3-Chloro-1,2,5-thiadiazol-4-yl)-1-
azabicyclo[2.2.2]octane oxalate

Hydrogenation for 48 h of 3-chloro-3-(3-chloro-1,2,5-thiadiazol-4-yl)-1-azabicyclo[2.2.2]octane (15.2 g, 66 mmol) in ethanol (500 ml) at 30 psi in the presence of 10% palladium on charcoal (2.0 g) gave, after filtration and evaporation, the hydrochloride salt of the wanted product in quantitative yield. Crystallization of a sample with oxalic acid from methanol/acetone/ether produced the title compound. (Compound 8). M.p. 207°–209° C.

EXAMPLE 6

3-(3-Ethoxy-1,2,5-thiadiazol-4-yl)-1-
azabicyclo[2.2.2]octane fumarate

Sodium (200 mg, 8.7 mmol) was dissolved in ethanol (30 ml) and 3-(3-chloro-1,2,5-thiadiazol-4-yl)-1-azabicyclo[2.2.2]octane (300 mg, 1.3 mmol) was added. The reaction mixture was stirred at 60° C. for 18 h. Water was added and the reaction mixture extracted with ether. The dried and filtrated ether extracts were evaporated to give the free base. Crystallization as the fumarate salt from isopropanol/ether gave the title compound in 210 mg yield. (Compound 9). M.p. 128°–131° C.

EXAMPLE 7

The following compounds were made in exactly the same manner as described in example 6 using the appropriate alcohol:
3-(3-Propoxy-1,2,5-thiadiazol-4-yl)-1-azabicyclo[2.2.2]octane fumarate. (Compound 10). M.p. 64°–67° C.
3-(3-Butoxy-1,2,5-thiadiazol-4-yl)-1-azabicyclo[2.2.2]octane oxalate. (Compound 46). M.p. 159°–160° C.

EXAMPLE 8

3-(3-Hexyloxy-1,2,5-thiadiazol-4-yl)-1-
azabicyclo[2.2.2]octane fumarate

A 50% dispersion of sodiumhydride (230 mg, 5 mmol) was dissolved in 1-hexanol (25 ml) and 3-(3-chloro-1,2,5-thiadiazol-4-yl)-1-azabicyclo[2.2.2]octane (250 mg, 1.1 mmol) was added. The reaction was stirred at 80° C. for 8 h and at room temperature for 18 h. After evaporation water was added to the residue and extracted with ether. The combined ether phases were dried and evaporated. Crystallization with fumaric acid from isopropanol/ether gave the title compound in 220 mg yield. (Compound 11). M.p. 108°–109° C.

The following compounds were made in exactly the same manner using the appropriate alcohol instead of 1-hexanol:
3-(3-(5-Hexenyloxy)-1,2,5-thiadiazol-4-yl)-1-azabicyclo[2.2.2]octane fumarate, M.p. 107°–110° C. (Compound 48).
3-(3-(3-Hexenyloxy)-1,2,5-thiadiazol-4-yl)-1-azabicyclo[2.2.2]octane fumarate, M.p. 135.5°–137.5° C. (Compound 49).
3-(3-Pentyloxy-1,2,5-thiadiazol-4-yl)-1-azabicyclo[2.2.2]octane oxalate, M.p. 102°–104° C. (Compound 50).
3-(3-Isopentyloxy-1,2,5-thiadiazol-4-yl)-1-azabicyclo[2.2.2]octane oxalate, M.p. 135.5°–137.5° C. (Compound 51).

EXAMPLE 9

3-(3-Pentylthio-1,2,5-thiadiazol-4-yl)-1-azabicyclo[2.2.2]octane fumarate

A solution of 3-(3-chloro-1,2,5-thiadiazol-4-yl)-1-azabicyclo[2.2.2]octane oxalate (500 mg, 1.56 mmol), sodium-hydrogen sulfide, monohydrate (463 mg, 6.25 mmol) and potassium carbonate (1.38 g, 10 mmol) in DMF (20 ml) was stirred at room temperature for 1 h. 1-Pentylbromide (755 mg, 5 mmol) was added, and the reaction mixture was stirred at room temperature for 18 h. 1N HCl was added, and the mixture extracted with ether once. 50% NaOH was added to the aqueous phase and extracted with ether. The ether phase was dried and evaporated. Crystallization of the residue with fumaric acid from isopropanol/ether gave the title compound in 380 mg yield. (Compound 12). M.p. 138°–139° C.

EXAMPLE 10

The following compounds were made in exactly the same manner as described in example 9, using the appropriate alkyl halogenide:
3-(3-Butylthio-1,2,5-thiadiazol-4-yl)-1-azabicyclo[2.2.2]octane fumarate. (Compound 13). M.p. 85°–87° C.
3-(3-Hexylthio-1,2,5-thiadiazol-4-yl)-1-azabicyclo[2.2.2]octane fumarate. (Compound 14). M.p. 138°–139° C.
3-(3-(3-Phenylpropylthio)-1,2,5-thiadiazol-4-yl)-1-azabicyclo[2.2.2]octane fumarate. (Compound 44). M.p. 123°–124° C.
3-(3-(4-Cyanobenzylthio)-1,2,5-thiadiazol-4-yl)-1-azabicyclo[2.2.2]octane oxalate. (Compound 45). M.p. 200° C. decomp.
3-(3-Ethylthio-1,2,5-thiadiazol-4-yl)-1-azabicyclo[2.2.2]octane oxalate, M.p. 194°–195° C. (Compound 52).
3-(3-Propylthio-1,2,5-thiadiazol-4-yl)-1-azabicyclo[2.2.2]octane oxalate, M.p. 206.5°–208° C. (Compound 53).
3-(3-Heptylthio-1,2,5-thiadiazol-4-yl)-1-azabicyclo[2.2.2]octane fumarate, .M.p. 130°–132° C. (Compound 54).

EXAMPLE 11

A. Ethyl (1-azabicyclo[3.2.1]octan-6-ylidene)cyano acetate

A solution of 1-azabicyclo[3.2.1]octan-6-one (41.25 g, 0.33 mol), acetic acid (2 ml), ammonium acetate (1.25 g) and ethyl cyanoacetate (37 g, 0.33 mol) in toluene (500 ml) was refluxed with a Dean-Stark water separator for 40 h. The toluene phase was extracted with 3×200 ml 5 M HCl solution. The water phase was basified with 28% ammonium hydroxide solution and extracted with ether (4×200 ml). The organic phases were dried over magnesium sulfate and evaporated. The residue was purified by column chromatography (eluent CH$_2$Cl$_2$/MeOH (9:1), yield 41 g of the title compound.

B. Ethyl (1-azabicyclo[3.2.1]octan-6-yl)cyanoacetate

A solution of ethyl (1-azabicyclo[3.2.1]octan-6-ylidene)cyanoacetate (41 g, 0.19 mol) in abs. ethanol (500 ml) was treated with 10% palladium on carbon (5 g) and hydrogen in a Parr shaker at 30 psi for 5 h. Filtration and evaporation gave the title compound in 36 g yield.

C. (1-azabicyclo[3.2.1]octan-6-yl)hydroxyiminoacetonitrile

Ethyl (1-azabicyclo[3.2.1]octan-6-yl)cyanoacetate (36 g, 0.16 mol) in abs. ethanol (100 ml) was added to a solution of sodium (4 g, 0.21 mol) in abs. ethanol (100 ml). Isoamylnitrite (25 ml, 0.19 mol) was added over 0.5 h, and the mixture was heated at 50° C. for 4 h. Evaporation of the reaction mixture gave crude sodium salt of the title compound, which was used without further purification.

D. 6-Chloro-6-(3-chloro-1,2,5-thiadiazol-4-yl)-1-azabicyclo[3.2.1]octane

A solution of crude (1-azabicyclo[3.2.1]octan-6-yl)hydroxyiminoacetonitrile (max. 0.16 mol) in DMF (150 ml) was added to a solution of S$_2$Cl$_2$ (50 ml, 0.68 mol) in DMF (100 ml) at 0° C. over 1 h. The reaction mixture was stirred over night and ice water (500 ml) was added. The mixture was filtered and the filter cake washed with 1 M HCl (3×100 ml). The water solution was extracted with ether (2×200 ml), then basified with a 28% ammonium hydroxide solution and extracted with ether (4×200 ml). The combined ether extracts from the last extraction were dried and evaporated. The residue was purified by column chromatography (eluent: CH$_2$Cl$_2$/MeOH (9:1)) to give the title compound in 11 g yield as a mixture of the endo and exo forms.

EXAMPLE 12

The following compound was made in exactly the same manner as described in example 11, starting from 1-azabicyclo[2.2.1]heptan-3-one: 3-Chloro-3-(3-chloro-1,2,5-thiadiazol-4-yl)-1-azabicyclo[2.2.1]heptane.

EXAMPLE 13

Exo-6-(3-chloro-1,2,5-thiadiazol-4-yl)-1-azabicyclo[3.2.1]octane and Endo-6-(3-chloro-1,2,5-thiadiazol-4-yl)-1-azabicyclo[3.2.1]octane-oxalate A solution of Endo/Exo-6-chloro-6-(3-chloro-1,2,5-thiadiazol-4-yl)-1-azabicyclo[3.2.1]octane (1.3 g, 5 mmol) in abs. ethanol (100 ml) was treated with 10% palladium on carbon (300 mg) in a Parr shaker at 20 psi for 4 h. The solution was filtered and evaporated. The residue was purified by column chromatography with CH$_2$Cl$_2$/MeOH/TEA (9:1:0.25). The first fraction contained the exo compound, which after crystallization with oxalic acid in acetone, was collected in 150 mg yield. (Compound 15). M.p. 148°–149° C.

The next fractions contained the endo compound, which after crystallization with oxalic acid from acetone was collected in 600 mg yield. (Compound 16). M.p. 195°–197° C.

EXAMPLE 14

Endo-6-(3-hexylthio-1,2,5-thiadiazol-4-yl)-1-azabicyclo[3.2.1]octane oxalate To a solution of endo-6-(3-chloro-1,2,5-thiadiazol-4-yl)-1-azabicyclo[3.2.1]octane (229 mg, 1.0 mmol) in DMF (10 ml) was added sodiumhydrogensulfide monohydrate (230 mg, 3.1 mmol). The reaction mixture was stirred at room temperature for 1 h. Potassium carbonate (1.38 g, 10 mmol) and 1-hexylbromide (335 mg, 2.5 mmol) was added and the mixture was stirred for 1 h. 1N HCl solution was added and the mixture extracted with ether (2×50 ml). The aqueous solution was basified with a 28% NH$_3$ solution and extracted with methylene chloride (3×100 ml). The methylene chloride phase was dried and evaporated. The residue was purified by column chromatography (eluent CH$_2$Cl$_2$/MeOH (9:1)). Crystallization of the pure base with oxalic acid from acetone gave the title compound in 100 mg yield. (Compound 17). M.p. 137°–139° C.

EXAMPLE 15

The following compounds were made in exactly the same manner as described in Example 14, using the appropriate alkyl bromide:
Endo-6-(3-(5-hexenylthio)-1,2,5-thiadiazol-4-yl)-1-azabicyclo[3.2.1]octane oxalate. (Compound 18). M.p. 113°–114° C.
Endo-6-(3-butylthio-1,2,5-thiadiazol-4-yl)-1-azabicyclo[3.2.1]octane oxalate. (Compound 24). M.p. 123°–124° C.
Endo-6-(3-ethylthio-1,2,5-thiadiazol-4-yl)-1-azabicyclo[3.2.1]octane oxalate. (Compound 25). M.p. 150°–151° C.
Endo-6-(3-pentylthio-1,2,5-thiadiazol-4-yl)-1-azabicyclo[3.2.1]octane oxalate. (Compound 26). M.p. 137°–138° C.
Endo-6-(3-(3-phenylpropylthio)-1,2,5-thiadiazol-4-yl)-1-azabicyclo[3.2.1]octane oxalate. (Compound 27). M.p. 127°–129° C.
Endo-6-(3-(4-cyanobenzylthio)-1,2,5-thiadiazol-4-yl)-1-azabicyclo[3.2.1]octane oxalate (Compound 28). M.p. 159°–161° C.
Endo-6-(3-propylthio-1,2,5-thiadiazol-4-yl)-1-azabicyclo[3.2.1]octane oxalate (Compound 57) M.p. 132°–134° C.

EXAMPLE 16

Exo-6-(3-ethoxy-1,2,5-thiadiazol-4-yl)-1-azabicyclo[3.2.1]octane oxalate and
Endo-6-(3-ethoxy-1,2,5-thiadiazol-4-yl)-1-azabicyclo[3.2.1]octane oxalate To a solution of sodium (230 mg, 10 mmol) in abs. ethanol (20 ml) was added endo-6-(3-chloro-1,2,5-thiadiazol-4-yl)-1-azabicyclo[3.2.1]octane (229 mg, 1 mmol). The reaction mixture was heated at 50° C. for 12 h and evaporated. Water (100 ml) was added, and the mixture was extracted with methylene chloride (4×50 ml). The organic phases were dried and evaporated. The residue was purified by column chromatography eluent (CH$_2$Cl$_2$ MeOH/TEA, 9:1:0.25). The first fractions contained the exo compound, which after crystallization with oxalic acid in acetone was collected in 50 mg yield. (Compound 19). M.p. 110°–112° C. The next fractions contained the endo compound, which after crystallization with oxalic acid in acetone was collected in 20 mg yield. (Compound 20). M.p. 127°–129° C.

EXAMPLE 17

Exo-3-(3-chloro-1,2,5-thiadiazol-4-yl)-1-azabicyclo[2.2.1]heptane oxalate and
Endo-3-(3-chloro-1,2,5-thiadiazol-4-yl)-1-azabicyclo[2.2.1]heptane oxalate A solution of endo/exo-3-chloro-3-(3-chloro-1,2,5-thiadiazol-4-yl)-1-azabicyclo[2.2.1]heptane (0.5 g, 2 mmol) in abs. ethanol (100 ml) was treated with 10% palladium on carbon in a Parr shaker at 20 psi for 4 h. The solution was filtered and evaporated. The residue was purified by column chromatography, eluent CH$_2$Cl$_2$/MeOH (9:1). The first fractions contained the exo compound, which after crystallization with oxalic acid from acetone/ether was collected in 50 mg yield. (Compound 21). M.p. 138°–140° C. The next fractions contained the endo compound, which after crystallization with oxalic acid from acetone, was collected in 450 mg yield. (Compound 22). M.p. 118°–121° C.

EXAMPLE 18

Endo-3-(3-methoxy-1,2,5-thiadiazol-4-yl)-1-azabicyclo[2.2.1]heptane oxalate

To a solution of sodium (110 mg, 5 mmol) in methanol (20 ml) was added endo-3-(3-chloro-1,2,5-thiadiazol-4-yl)-1-azabicyclo[2.2.1]heptane (110 mg, 0.5 mmol). The reaction mixture was heated at reflux for 60 h and evaporated. Water (50 ml) was added, and the mixture was extracted with methylene chloride (4×50 ml). The organic phases were dried and evaporated. The residue was purified by column chromatography eluent (CH$_2$Cl$_2$/MeOH, 9:1). Crystallization of the free base with oxalic acid from acetone/ether gave the title compound in 40 mg yield. (Compound 23). M.p. 104°–106° C.

EXAMPLE 19

Exo-6-(3-hexylthio-1,2,5-thiadiazol-4-yl)-1-azabicyclo[3.2.1]octane oxalate

To a solution of exo-6-(3-chloro-1,2,5-thiadiazol-4-yl)-1-azabicyclo[3.2.1]octane (229 mg, 1.0 mmol) in DMF (20 ml) was added sodiumhydrogensulfide monohydrate (230 mg, 3.0 mmol). The reaction mixture was stirred at room temperature for 1 h. Potassium carbonate (1.38 g, 10 mmol) and 1-hexylbromide (335 mg, 2.5 mmol) was added and the mixture was stirred for 1 h. 1N HCl solution was added and the mixture extracted with ether (2×50 ml). The aqueous solution was basified with a 28% NH$_3$ solution and extracted with ether (2×50 ml). The ether phase was dried and evaporated. The residue was crystallized as the oxalate salt from acetone/ether in 200 mg yield. ( Compound 29). M.p. 118°614 119° C.

EXAMPLE 20

The following compounds were made in exactly the same manner as described in example 19, using the appropriate alkylbromide:
Exo-6-(3-butylthio-1,2,5-thiadiazol-4-yl)-1-azabicyclo[3.2.1]octane oxalate. (Compound, 30). M.p. 143°–145° C.
Exo-6-(3-pentylthio-1,2,5-thiadiazol-4-yl)-1-azabicyclo[3.2.1]octane oxalate. (Compound 31 ). M.p. 117°–118° C.
Exo-6-(3-ethylthio-1,2,5-thiadiazol-4-yl)-1-azabicyclo[3.2.1]octane oxalate. (Compound 32). M.p. 159°–160° C.
Exo-6-(3-propylthio-1,2,5-thiadiazol-4-yl)-1-azabicyclo[3.2.1]octane oxalate (Compound 58), M.p. 173°–174° C.

EXAMPLE 21

Endo-3-(3-pentylthio-1,2,5-thiadiazol-4-yl)-1-azabicyclo[2.2.1]heptane fumarate

To a solution of endo-3-(3-chloro-1,2,5-thiadiazol-4-yl)-1-azabicyclo[2.2.1]heptane (215 mg, 1.0 mmol) in DMF (20 ml) was added sodium hydrogensulfide monohydrate (230 mg, 3.0 mmol). The reaction mixture was stirred at room temperature for 1 h. Potassium carbonate (1.38 g, 10 mmol) and 1-pentylbromide (0.45 g, 3 mmol) was added and the mixture was stirred for 1 h. 1 M hydrochloric acid solution (100 ml) was added and the mixture extracted with ether (2×50 ml). The aqueous solution was basified with a 28% NH$_3$-solution and extracted with ether (3×75 ml). The ether phase was dried and evaporated. The residue was crystallized as the fumarate salt from MeOH/ether in 250 mg yield. (Compound 33). M.p. 120°–122° C.

EXAMPLE 22

The following compounds were made in exactly the same manner as described in example 21 using the appropriate alkylbromide:
Endo-3-(3-hexylthio-1,2,5-thiadiazol-4-yl)-1-azabicyclo [2.2.1]heptane fumarate. (Compound 34). M.p. 127°–129° C.
Endo-3-(3-(3-phenylpropylthio)-1,2,5-thiadiazol-4-yl)-1-azabicyclo[2.2.1]heptane oxalate. (Compound 35). M.p. 119°–120° C.
Endo-3-(3-butylthio-1,2,5-thiadiazol-4-yl)-1-azabicyclo [2.2.1]heptane fumarate. (Compound 36). M.p. 106°–108° C.
Endo:3-(3-propylthio-1,2,5-thiadiazol-4-yl)-1-azabicyclo [2.2.1]heptane oxalate. (Compound 37). M.p. 169°–170° C.

EXAMPLE 23

Exo-3-(3-pentylthio-1,2,5-thiadiazol-4-yl)-1-azabicyclo[2.2.1]heptane oxalate

To a solution of exo-3-(3-chloro-1,2,5-thiadiazol-4-yl)-1-azabicyclo[2.2.1]heptane (215 mg, 1.0 mmol) in DMF (20 ml) was added sodium hydrogensulfide monohydrate (230 mg, 3.0 mmol). The reaction mixture was stirred at room temperature for 1 h. Potassium carbonate (1.38 g, 10 mmol) and 1-pentylbromide (0.45 g, 3 mmol) was added and the mixture was stirred for 1 h. 1 M hydrochloric acid solution (100 ml) was added and the mixture extracted with ether (2×ml). The aqueous solution was basified with a 28% NH$_3$-solution and extracted with ether (3×75 ml). The ether phase was dried and evaporated. The residue was crystallized as the oxalate salt from MeOH/ether in 250 mg yield. (Compound 38). M.p. 120°–122° C.

EXAMPLE 24

The following compounds were made in exactly the same manner as described in example 23, using the appropriate alkylbromide:
Exo-3-(3-hexylthio-1,2,5-thiadiazol-4-yl)-1-azabicyclo [2.2.1]heptane oxalate. (Compound 39). M.p. 102°–103° C.
Exo-3-(3-propylthio-1,2,5-thiadiazol-4-yl)-1-azabicyclo [2.2.1]heptane oxalate. (Compound 40). M.p. 132°–133° C.
Exo-3-(3-(3-phenylpropylthio)-1,2,5-thiadiazol-4-yl)-1-azabicyclo[2.2.1]heptane oxalate. (Compound 41). M.p. 126°–127° C.
Exo-3-(3-butylthio-1,2,5-thiadiazol-4-yl)-1-azabicyclo [2.2.1]heptane oxalate. (Compound 42). M.p. 188°–189° C.

EXAMPLE 25

A. 8-Ethoxycarbonyl-3-chloro-2-formyl-8-azabicyclo[3.2.1]oct-2-ene

To a solution of dry DMF (45 g, 0.6 mol) in dry CH$_2$Cl$_2$ (150 ml) was added POCl$_3$ (75 g, 0.5 mol) at 0°–10° C. 8-Ethoxycarbonyl-8-azabicyclo[3.2.1]octane-3-one (57 g, 0.29 mol) dissolved in dry CH$_2$Cl$_2$ (60 ml) was added. The reaction mixture was stirred over night at room temperature, then added to ice water (1.000 ml). The phases were separated and the water phase extracted with CH$_2$Cl$_2$ (2×200 ml). The combined CH$_2$Cl$_2$ extracts were washed with a saturated NaHCO$_3$ solution and water, dried and evaporated to give 70 g of the title compound, which was used in the next step without further purification.

B. 8-Ethoxycarbonyl-3-chloro-2-(3-chloro-1,2,5-thiadiazol-4-yl)-8-azabicyclo [3.2.1]oct-2-ene Potassium cyanide (8.5 g, 0.13 mol) and ammonium chloride (6.4 g, 0.12 mol) were dissolved in a min. amount of water. 8-Ethoxycarbonyl-3-chloro-2-formyl-8-azabicyclo [3.2.1]oct-2-ene (23 g, 0.1 mol) dissolved in DMF (25 ml) was added. The reaction mixture was stirred at room temperature for 3 days, then added to a 5 N hydrochloric acid solution (200 ml). The aqueous phase was extracted with ether (3×75 ml), then basified with a 28% NH$_3$ solution and extracted with ether (4×100 ml). The ether phases from the last extraction were dried, evaporated and dissolved in DMF (50 ml). This solution was added to sulphur monochloride (16.8 g, 0.12 mol) in DMF (50 ml). The reaction mixture was stirred over night at room temperature and poured into ice-water. The water phase was extracted with ether (3×100 ml). The combined ether phases were dried and evaporated. The residue was purified by column chromatography (eluent: CH$_2$Cl$_2$). Yield 3.2 g as an oil.

EXAMPLE 26

3-Chloro-2-(3-ethoxy-1,2,5-thiadiazol-4-yl)-8-azabicyclo[3.2.1]oct-2-ene oxalate To a solution of sodium (230 mg, 10 mmol) in abs. ethanol (50 ml) was added 8-ethoxycarbonyl-3-chloro-2-(3-chloro-1,2,5-thiadiazol-4-yl)-8-azabicyclo[3.2.1]oct-2-ene (670 mg, 2 mmol). The reaction mixture was heated at reflux overnight, evaporated and conc. HCl (40 ml) was added. The reaction mixture was heated at reflux for 4 days, evaporated and basified with a 28% NH$_3$ solution. The aqueous solution was extracted with ether (3×75 ml). The combined ether extracts were dried and evaporated. The residue was purified by column chromatography (eluent CH$_2$Cl$_2$/MeOH;9:1). Crystallization of the free base with oxalic acid in acetone gave the title compound in 110 mg yield. (Compound 43). M.p. 178°–180° C.

EXAMPLE 27

3-Chloro-2-(3-chloro-1,2,5-thiadiazol-4-yl)-8-azabicyclo[3.2.1]oct-2-ene oxalate To a solution of 8-Ethoxycarbonyl-3-chloro-2-(3-chloro-1,2,5-thiadiazol-4-yl)-8-azabicyclo[3.2.1]oct-2-ene (1.7 g, 5 mmol) in dry toluene (50 ml) was added AlCl$_3$ (2.6 g, 20 mmol). The reaction mixture was slowly heated to 80° C. and kept at this temperature for 10 min. After cooling to room temperature the reaction mixture was poured on ice and basified with a 50% NaOH solution. The aqueous phase was extracted with CH$_2$Cl$_2$ (3×100 ml). The combined organic extracts were dried over MgSO$_4$ and evaporated. The residue was crystallized as the oxalate salt from acetone to give the title compound. Yield 1.6 g (Compound 47), M.p. 194°–195° C.

EXAMPLE 28

The following compounds were made in exactly the same manner as described in Example 16 using the appropriate alcohol:

Exo-6-(3-pentyloxy-1,2,5-thiadiazol-4-yl)-1-azabicyclo [3.2.1]octane oxalate (Compound 59), M.p. 122°–123° C.
Endo-6-(3-pentyloxy-1,2,5-thiadiazol-4-yl)-1-azabicyclo [3.2.1]octane oxalate (Compound 60), M.p. 124°–125° C.

EXAMPLE 29

A. 4-Chloro-3-formyl-1-azabicyclo[3.3.1]non-2-ene

To DMF (50 ml, 0.68 mol) was slowly added $POCl_3$ (50 ml, 0.54 mol) at 0° C. over 1 h. 1-Azabicyclo[3.3.1]nonane-4-one hydrochloride (17.5 g, 0.1 mol) was added in one portion and the reaction mixture heated at 100° C. for 1 h. After cooling the reaction mixture was poured on ice (1000 g) and the reaction mixture neutralized with potassium carbonate. The water phase was extracted with ether (5×200 ml). The organic phase was dried over $MgSO_4$ and evaporated. The residue was purified by column chromatography (eluent: $CH_2Cl_2/CH_3OH$ (9:1)), yielding 17 g of the title compound.

B. 4-Chloro-3-(3-chloro-1,2,5-thiadiazol-4-yl)-1-azabicyclo[3.3.1]non-3-ene oxalate To a solution of oxalic acid (9.0 g, 100 mmol) in water (100 ml) was added 4-chloro-3-formyl-1-azabicyclo[3.3.1]non-2-ene (17.0 g, 95 mmol). Potassium cyanide (6.8 g, 10 mmol) dissolved in a min. amount of water was added dropwise. The reaction mixture was stirred at room temperature for 2 h. The precipitated crystals were filtered and suspended in water/EtOH (4:1, 120 ml). Ammonium chloride (6.0 g, 100 mmol) and ammonium hydroxide (28% in water 10 ml) was added and the reaction mixture was stirred at room temperature overnight. The water phase was extracted with methylene chloride (5×100 ml). The organic phases were dried over magnesium sulphate and evaporated. The residue was dissolved in DMF (50 ml) and added dropwise to a solution of sulfurmonochloride (20 ml, 250 mmol) in DMF (30 ml) at 0° C. The reaction mixture was stirred at room temperature for 4 h, then crushed ice (500 g) was added. The precipitated sulfur was filtered off and the filtrate washed with 1 M hydrochloric acid solution (2×100 ml) the combined water phases was basified with ammonia (28% in water) and extracted with ether (4×200 ml). The combined organic phases were dried and evaporated. The residue was crystallized as the oxalate salt from acetone/ether to give the title compound. Yield 10.8 g (Compound 61), M.p. 149°–150° C.

EXAMPLE 30

4-Chloro-3-(3-propyloxy-1,2,5-thiadiazol-4-yl)-1-azabicyclo[3.3.1]non-3-ene oxalate To a solution of sodium (0.23 g, 10 mmol) in n-propanol (10 ml) was added 4-chloro-3-(3-chloro-1,2,5-thiadiazol-4-yl)-1-azabicyclo[3.3.1]non-3-ene (0.274 g, 1 mmol). The reaction mixture was heated at 60° C. for 2 h. Hydrochloric acid (1 M, 100 ml) was added, and the water phase extracted with ether (2×50 ml). The water phase was basified with solid potassium carbonate and extracted with ether (3×75 ml). The combined ether extracts were dried over magnesium sulfate and evaporated. The residue was crystallized as the oxalate salt from acetone/ether to give the title compound. Yield 180 mg (Compound 62), M.p. 122°–123° C.

EXAMPLE 31

The following compounds were made in exactly the same manner as described in example 30 using the appropriate alcohol:
4-Chloro-3-(3-pentyloxy-1,2,5-thiadiazol-4-yl)-1-azabicyclo[3.3.1]non-3-ene oxalate (Compound 63), M.p. 114°–115° C.
4-Chloro-3-(3-methoxy-1,2,5-thiadiazol-4-yl)-1-azabicyclo [3.3.1]non-3-ene oxalate (Compound 64), M.p. 103°–104° C.

EXAMPLE 32

4-Chloro-3-(1,2,5-thiadiazol-4-yl)-1-azabicyclo[3.3.1]non-3-ene oxalate

To a solution of sodium (0.092 g, 4 mmol) in isopropanol (40 ml) was added n-butylmercaptan (270 ml, 3 mmol). 4-Chloro-3-(3-chloro-1,2,5-thiadiazol-4-yl)-1-azabicyclo [3.3.1]non-3-ene (0.82 g, 3 mmol) dissolved in isopropanol (10 ml) was added and the reaction mixture was stirred overnight at room temperature. The reaction mixture was evaporated and hydrochloric acid (1 M, 100 ml) was added. The water phase was extracted with ether (2×50 ml) basified with solid potassium carbonate and extracted with ether (3×75 ml). The organic phase was dried and evaporated. The residue was purified by column chromatography (eluent: ethyl acetate) and the free base was crystallized with oxalic acid from acetone to give the title compound. Yield 250 mg (Compound 65) M.p. 175°–77° C.

EXAMPLE 33

(−) 3-(3-Butylthio-1,2,5-thiadiazol-4-yl)-1-azabicyclo[2.2.2]octane (+) L-tartrate To a solution of 3-(3-butylthio-1,2,5-thiadiazol-4-yl)-1-azabicyclo[2.2.2]octane (free base of compound 13, example 10) (5.5 g, 19.43 mmol) in ethanol (50 ml) was added a solution of (+)L-tartaric acid (2.9 g, 19.4 mmol) in water (10 ml). Ether (approx. 200 ml) was added to the solution to give a slightly unclear solution. The title compound was precipitated overnight and the crystals collected by filtration (3.05 g). Recrystallization twice from ethanol (20 ml) and ether gave the pure (−) enantiomer (1.90 g) (Compound 55), M.p. 106°–108° C. [α](free base)=−15.80° (C=4.05 MeOH).

EXAMPLE 34

(+) 3-(3-Butylthio-1,2,5-thiadiazol-4-yl)-1-azabicyclo[2.2.2]octane (−)D-tartrate The mother liquour from the crystallization with (+)L-tartaric acid (example 33) was evaporated and the residue treated with 50% NaOH in water and extracted with ether. The combined ether phase were dried and evaporated to give crude free base of the title compound (2.9 g, 10.2 mmol). The residue was dissolved in ethanol (15 ml) and a solution of (−) D-tartaric acid (1.54 g, 10.2 mmol) in water (4 ml) was added. Ether was added to the solution and the title compound precipitated overnight. The crystals were collected by filtration and recrystallization twice from ethanol/ether gave the pure (+) enantiomer (1.90 g) (Compound 56), M.p. 106°–108° C. [α](free base)=+14.94° (C=4.09 in MeOH).

EXAMPLE 35

3-(3-Amino-1,2,5-oxadiazol-4-yl)-1-azabicyclo[2.2.2]octane fumarate

To a solution of crude (1-azabicyclo[2.2.2]octan-3-yl)hydroxyiminoacetonitrile (10 g, max. 29 mmol) (example 1C) in methanol (50 ml) was added a methanol solution of hydroxylamine (prepared from $NH_2OH$, HCl (4.2 g, 60 mmol) in methanol (60 ml) and sodium (1.38 g, 60 mmol) in methanol (60 ml)). The reaction mixture was stirred at 40° C. for 18 h and evaporated to give the crude amide oxime derivative. The residue was treated with excess of $POCl_3$ at 45° C. for 18 h. Water and sodium hydroxide was added to obtain alkaline pH and the aqueous mixture extracted with chloroform. The combined organic phases were dried and evaporated to give the free base of the title compound as a solid (yield 570 mg). MS: $M^+$: 194. Crystallization as the fumarate salt from isopropanol gave the title compound (110 mg) (Compound 66), M.p. 60°–75° C.

EXAMPLE 36

A. 5-Carboxaldehyde-1-azabicyclo[3.2.1]octane

To a solution of 1-azabicyclo[3.2.1]oct-5-yl-N-methyl-N-methoxycarboxamide (4.0 g, 17.4 mmol) in tetrahydrofuran (100 ml) was added dropwise a 1 Molar solution of DIBAL (26 ml, 26 mmol) at −65° C. The temperature of the reaction mixture was allowed to raise to 0° C. over 30 min. and then cooled to −65° C. Aqueous hydrochloric acid (75 ml, 5N) was added to the cold reaction mixture and the tetrahydrofuran was evaporated in vacuo. The aqueous residue was stirred overnight at room temperature and then evaporated. Water and potassium carbonate was added to the residue and extracted with methylene chloride (3×300 ml). The combined methylene chloride phases were dried and evaporated to give the title compound as an oil. Yield 2.75 g.

B. 2-Amino-2-(1-azabicyclo[3.2.1]oct-5-yl)acetonitrile

To a solution of potassium cyanide (1.43 g, 22 mmol) in water (20 ml) 5-carboxaldehyde-1-azabicyclo[3.2.1]octane (2.75 g, 19.8 mmol) was added over 30 min. at 0°–10° C. Acetic acid (1.26 ml, 22 mmol) was added to the reaction mixture over 30 min. at 5°–10° C. The reaction mixture was stirred at room temperature for further 18 h and cooled to 5° C. Aqueous sodium hydroxide was added to obtain alkaline pH and then extracted with methylene chloride (3×200 ml). The combined organic phases were evaporated and the residue was treated with a solution of ammonium chloride (3.8 g, 72 mmol) in water (10 ml) and 25% aqueous ammonia (5 ml). The reaction mixture was stirred at room temperature for 18 h and then extracted with methylene chloride. The combined organic phases were dried and evaporated to give the title compound. Yield. 1.67 g.

C. 5-(3-Chloro-1,2,5-thiadiazol-4-yl)-1-azabicyclo[3.2.1]octane oxalate

2-Amino-2-(1-azabicyclo[3.2.1]oct-5-yl)acetonitrile (1.67 g, 10 mmol) was dissolved in DMF (10 ml) and a solution of sulfur monochloride (2.57 ml, 30 mmol) in DMF (10 ml) was added dropwise at 0° C. The reaction mixture was stirred at room temperature for 18 h and cooled to 0° C. whereupon water (40 ml) and aqueous potassium hydroxide was added slowly. The alkaline reaction mixture was extracted with ether (3×300 ml) and the combined ether phases were dried and evaporated. The residue (850 mg) was crystallized with oxalic acid from acetone/methanol to give the title compound. Yield 710 mg (Compound 67), M.p. 137.5°–139.5° C.

EXAMPLE 37

5-(3-Hexylthio-1,2,5-thiadiazol-4-yl)-1-azabicyclo[3.2.1]octane oxalate

Sodium hydrosulfide monohydrate (326 mg, 4.4 mmol) was added to a solution of 5-(3-chloro-1,2,5-thiadiazol-4-yl)-1-azabicyclo[3.2.1]octane oxalate (350 mg, 1.1 mmol) in DMF (20 ml) at room temperature and the reaction mixture was stirred for 30 min. Potassium carbonate (1.24 g, 9 mmol) and 1-bromohexane (561 µl, 4 mmol) were added and the reaction mixture was stirred for 3 h. Water (50 ml) was added to the reaction mixture and the aqueous phase extracted with ether (3×200 ml). The combined ether phases were dried and evaporated to give the crude free base of the title compound (220 mg). The residue was crystallized as the oxalate salt from acetone to give the title compound. Yield 200 mg (Compound 68), M.p. 67°–69° C.

EXAMPLE 38

Exo-3-(3-methylthio-1,2,5-thiadiazol-4-yl)-1-azabicyclo[2.2.1]heptane oxalate To a solution of exo-3-(3-chloro-1,2,5-thiadiazol-4-yl)-1-azabicyclo[2.2.1]heptane (215 mg, 1.0 mmol) in DMF (20 ml) was added sodiumhydrogensulfide monohydrate (230 mg, 3.0 mmol). The reaction mixture was stirred at room temperature for 1 h. Potassium carbonate (1.38 g, 10 mmol) and methyliodide (0.42 g, 3 mmol) were added and the mixture stirred at room temperature for 0.5 h. 1N hydrochloric acid solution (100 ml) was added and extracted with ether (2×50 ml). The aqueous solution was basified with a 28% $NH_3$ solution and extracted with ether (3×75 ml). The combined ether phases were dried and evaporated. The residue was crystallized as the oxalate salt from acetone in 180 mg yield. (Compound 69). M.p. 133°–139° C.

EXAMPLE 39

The following compounds was made in exactly the same manner as described in example 38, using ethyliodide:
Exo-3-(3-ethylthio-1,2,5-thiadiazol-4-yl)-1-azabicyclo[2.2.1]heptane oxalate from ethyliodide and exo-3-(3-chloro-1,2,5-thiadiazol-4-yl)-1-azabicyclo[2.2.1]heptane. (Compound 70). M.p. 156°–157° C.
Exo-3-(3-(4-cyanobenzylthio)-1,2,5-thiadiazol-4-yl)-1-azabicyclo[2.2.1]heptane oxalate from exo-3-(3-chloro-1,2,5-thiadiazol-4-yl)-1-azabicyclo[2.2.1]heptane and 4-cyanobenzylchloride. (Compound 173). M.p. 200°–201° C.

EXAMPLE 40

The following compounds were made in exactly the same manner as described in example 38 using endo 3-(3-chloro-1,2,5-thiadiazol-4-yl)-1-azabicyclo[2.2.1]heptane and the appropriate alkylhalogenide.
Endo-3-(3-(2-phenoxyethylthio)-1,2,5-thiadiazol-4-yl)-1-azabicyclo[2.2.1]heptane oxalate from 2-phenoxyethylbromide and endo 3-(3-chloro-1,2,5-thiadiazol-4-yl)-1-azabicyclo[2.2.1]heptane. (Compound 71). M.p. 127°–130° C.
Endo-3-(3-(2-thienyl)propylthio-1,2,5-thiadiazol-4-yl)-1-azabicyclo[2.2.1]heptane oxalate from 1-chloro-3-(2-thienyl)propane and endo-3-(3-chloro-1,2,5-thiadiazol-4-yl)-1- azabicyclo[2.2.1]heptane. (Compound 72). M.p. 123°–126° C.

Endo-3-(3-(2-phenylthio)ethylthio-1,2,5-thiadiazol-4-yl)-1-azabicyclo[2.2.1]heptan oxalate from 1-chloro-2-(phenylthio)ethane and endo-3-(3-chloro-1,2,5-thiadiazol-4-yl)-1-azabicyclo[2.2.1]heptane. (Compound 73). M.p. 143°–145° C.

Endo-3-(3-(4-cyanobenzylthio)-1,2,5-thiadiazol-4-yl)-1-azabicyclo[2.2.1]heptane oxalate from endo-3-(3-chloro-1,2,5-thiadiazol-4-yl)-1-azabicyclo[2.2.1]heptane and 4-cyanobenzylchloride. (Compound 174). M.p. 165°–167° C.

EXAMPLE 41

Exo-6-(3-methylthio-1,2,5-thiadiazol-4-yl)-1-azabicyclo[3.2.1]octane oxalate

To a solution of exo-6-(3-chloro-1,2,5-thiadiazol-4-yl)-1-azabicyclo[3.2.1]octane (229 mg, 1.0 mmol) in DMF (20 ml) was added sodiumhydrogensulfide monohydrate (230 mg, 3.0 mmol). The reaction mixture was stirred at room temperature for 1 h. Potassium carbonate (1.38 g, 10 mmol) and methyliodide (0.42 g, 3 mmol) were added and the mixture stirred for 1 h. 1 N hydrochloric acid solution (100 ml) was added and the mixture extracted with ether (2×50 ml). The aqueous solution was basified with a 28% $NH_3$ solution and extracted with ether (3×75 ml). The combined ether phases were dried and evaporated. The residue was crystallized as the oxalate salt from acetone in 200 mg yield. (Compound 74). M.p. 141°–142° C.

EXAMPLE 42

The following compounds were made in exactly the same manner as described in example 41 using the appropriate alkylhalogenide:

Exo-6-(3-heptylthio-1,2,5-thiadiazol-4-yl)-1-azabicyclo[3.2.1]octane oxalate from exo-6-(3-chloro-1,2,5-thiadiazol-4-yl)-1-azabicyclo[3.2.1]octane and 1-bromoheptane. (Compound 75). M.p. 111°–112° C.

Exo-6-(3-isohexylthio-1,2,5-thiadiazol-4-yl)-1-azabicyclo[3.2.1]octane oxalate from exo-6-(3-chloro-1,2,5-thiadiazol-4-yl)-1-azabicyclo[3.2.1]octane and 1-bromo-4-methylpentane. (Compound 76). M.p. 128°–130° C.

Exo-6-(3-isopentylthio-1,2,5-thiadiazol-4-yl)-1-azabicyclo[3.2.1]octane from exo-6-(3-chloro-1,2,5-thiadiazol-4-yl)-1-azabicyclo[3.2.1]octane and 1-bromo-3-methylbutane. (Compound 77). M.p. 130°–132° C.

Exo-6-(3-(4-cyanobutylthio)-1,2,5-thiadiazol-4-yl)-1-azabicyclo[3.2.1]octane oxalate from exo-6-(3-chloro-1,2,5-thiadiazol-4-yl)-1-azabicyclo[3.2.1]octane and 1-bromo-4-cyanobutane. (Compound 78). M.p. 148°–150° C.

Exo-6-(3-cyanomethylthio-1,2,5-thiadiazol-4-yl)-1-azabicyclo[3.2.1]octane oxalate from exo-6-(3-chloro-1,2,5-thiadiazol-4-yl)-1-azabicyclo[3.2.1]octane and chloroacetonitrile. (Compound 79). M.p. 141°–142° C.

Exo-6-(3-(2-cyanoethylthio)-1,2,5-thiadiazol-4-yl)-1-azabicyclo[3.2.1]octane oxalate from exo-6-(3-chloro-1,2,5-thiadiazol-4-yl)-1-azabicyclo[3.2.1]octane and 1-bromo-2-cyanoethane. (Compound 80). M.p. 151°–152° C.

Exo-6-(3-(3-cyanopropylthio)-1,2,5-thiadiazol-4-yl)-1-azabicyclo[3.2.1]octane oxalate from exo-6-(3-chloro-1,2,5-thiadiazol-4-yl)-1-azabicyclo[3.2.1]octane and 1-bromo-3-cyanopropane. (Compound 81). M.p. 114°–115° C.

Exo-6-(3-(4-cyanobenzylthio)-1,2,5-thiadiazol-4-yl)-1-azabicyclo[3.2.1]octane oxalate from exo-6-(3-chloro-1,2,5-thiadiazol-4-yl)-1-azabicyclo[3.2.1]octane and 4-cyanobenzylchloride. (Compound 82). M.p. 198°–199° C.

Exo-6-(3-(3-phenylpropylthio)-1,2,5-thiadiazol-4-yl)-1-azabicyclo[3.2.1]octane oxalate from exo-6-(3-chloro-1,2,5-thiadiazol-4-yl)-1-azabicyclo[3.2.1]octane and 1-bromo-3-phenylpropane. (Compound 83). M.p. 149°–150° C.

Exo-6-(3-(2-phenoxyethylthio)-1,2,5-thiadiazol-4-yl)-1-azabicyclo[3.2.1]octane oxalate from exo-6-(3-chloro-1,2,5-thiadiazol-4-yl)-1-azabicyclo[3.2.1]octane and 1-bromo-2-phenoxyethane. (Compound 133). M.p. 137°–144° C.

Exo-6-(3-benzylthio-1,2,5-thiadiazol-4-yl)-1-azabicyclo[3.2.1]octane oxalate from exo-6-(3-chloro-1,2,5-thiadiazol-4-yl)-1-azabicyclo[3.2.1]octane and benzylchloride. (Compound 134). M.p. 153°–155° C.

EXAMPLE 43

The following compounds were made in exactly the same manner as described in example 41 by reacting endo-6-(3-chloro-1,2,5-thiadiazol-4-yl)-1-azabicyclo[3.2.1]octane with the appropriate alkylhalogenide:

Endo-6-(3-(2-phenoxyethylthio)-1,2,5-thiadiazol-4-yl)-1-azabicyclo[3.2.1]octane oxalate from endo-6-(3-chloro-1,2,5-thiadiazol-4-yl)-1-azabicyclo[3.2.1]octane and 1-bromo-2-phenoxyethane. (Compound 84). M.p. 150°–155° C.

Endo-6-(3-methylthio-1,2,5-thiadiazol-4-yl)-1-azabicyclo[3.2.1]octane oxalate from endo-6-(3-chloro-1,2,5-thiadiazol-4-yl)-1-azabicyclo[3.2.1]octane and methyliodide. (Compound 85). M.p. 150°–151° C.

Endo-6-(3-isopentylthio-1,2,5-thiadiazol-4-yl)-1-azabicyclo[3.2.1]octane oxalate from endo-6-(3-chloro-1,2,5-thiadiazol-4-yl)-1-azabicyclo[3.2.1]octane and 1-bromo-3-methylbutane. (Compound 86). M.p. 118°–120° C.

Endo-6-(3-isohexylthio-1,2,5-thiadiazol-4-yl)-1-azabicyclo[3.2.1]octane oxalate from endo-6-(3-chloro-1,2,5-thiadiazol-4-yl)-1-azabicyclo[3.2.1]octane and 1-bromo-4-methylpentane. (Compound 87). M.p. 110°–112° C.

Endo-6-(3-benzylthio-1,2,5-thiadiazol-4-yl)-1-azabicyclo[3.2.1]octane oxalate from endo-6-(3-chloro-1,2,5-thiadiazol-4-yl)-1-azabicyclo[3.2.1]octane and benzylchloride. (Compound 88). M.p. 110°–112° C.

Endo-6-(3-cyanomethylthio-1,2,5-thiadiazol-4-yl)-1-azabicyclo[3.2.1]octane oxalate from endo-6-(3-chloro-1,2,5-thiadiazol-4-yl)-1-azabicyclo[3.2.1]octane and chloroacetonitrile. (Compound 89). M.p. 158°–59° C.

Endo-6-(3-(2-cyanoethylthio)-1,2,5-thiadiazol-4-yl)-1-azabicyclo[3.2.1]octane oxalate from endo-6-(3-chloro-1,2,5-thiadiazol-4-yl)-1-azabicyclo[3.2.1]octane and 1-bromo-2-cyanoethane. (Compound 90). M.p. 160°–161° C.

Endo-6-(3-(3-cyanopropylthio)-1,2,5-thiadiazol-4-yl)-1-azabicyclo[3.2.1]octane oxalate from endo-6-(3-chloro-1,2,5-thiadiazol-4-yl)-1-azabicyclo[3.2.1]octane and 1-bromo-3-cyanopropane. (Compound 91). M.p. 119°–120° C.

Endo-6-(3-(4-cyanobutylthio)-1,2,5-thiadiazol-4-yl)-1-azabicyclo[3.2.1]octane oxalate from endo-6-(3-chloro-1,2,5-thiadiazol-4-yl)-1-azabicyclo[3.2.1]octane and 1-bromo-4-cyanobutane. (Compound 92). M.p. 150°–151° C.

EXAMPLE 44

4-Chloro-3-(3-butoxy-1,2,5-thiadiazol-4-yl)-1-azabicyclo[3.3.1]non-3-ene oxalate To a solution of sodium (0.23 g, 10 mmol) in n-butanol (10 ml) was added 4-chloro-3-(3-chloro-1,2,5-thiadiazol-4-yl)-1-azabicyclo[3.3.1]non-3-ene (Compound 61) (0.274 g, 1 mmol). The reaction mixture was heated at 60° C. for 4 h. Water (100 ml) was added and the water phase extracted with ether (3×50 ml). The combined ether extracts were dried over magnesium sulfate and evaporated. The residue was crystallized from acetone/ether to give the title compound in 200 mg yield. (Compound 93). M.p. 104°–107° C.

EXAMPLE 45

4-Chloro-3-(3-hexyloxy-1,2,5-thiadiazol-4-yl)-1-azabicyclo[3.3.1]non-3-ene hydrochloride The compound was made as described in example 44 by reacting 4-chloro-3-(3-chloro-1,2,5-thiadiazol-4-yl)-1-azabicyclo[3.3.1]non-3-ene with 1-hexanol. The free base was crystallized as the hydrochloride from ether. (Compound 94). M.p. 100°–101° C.

EXAMPLE 46

3-(3-Butoxy-1,2,5-thiadiazol-4-yl)-1-azabicyclo[3.3.1]non-3-ene oxalate

To a solution of 4-chloro-3-(3-butoxy-1,2,5-thiadiazol-4-yl)-1-azabicyclo[3.3.1]non-3-ene (0.63 g, 2.0 mmol) in abs. ethanol (20 ml), triethyl amine (3 ml) and formic acid (1 ml) were added. The reaction mixture was heated to 80° C. under nitrogen. At this temperature palladium on carbon (0.5 g, 5%) was added in one portion. After 15 min. another portion of palladium on carbon (0.25 g, 5%) was added. The last addition of palladium on carbon was repeated twice. After cooling, the reaction mixture was filtered and evaporated., The residue was dissolved in water basified with potassium carbonate and extracted with ether (3×75 ml). The ether extracts were dried and evaporated. The crude compound was purified by column chromatography (eluent: $CH_2Cl_2$/MeOH (9:1)), yielding 80 mg of free base. The title compound was crystallized with oxalic acid from acetone/ether in 80 mg yield. (Compound 95). M.p. 150°–151° C.

EXAMPLE 47

The following compounds were prepared in exactly the same manner as described in example 46.
3-(3-Methoxy-1,2,5-thiadiazol-4-yl)-1-azabicyclo[3.3.1]non-3-ene oxalate from 4-chloro-3-(3-methoxy-1,2,5-thiadiazol-4-yl)-1-azabicyclo[3.3.1]non-3-ene. (Compound 96). M.p. 200°–201° C.
3-(3-Propoxy-1,2,5-thiadiazol-4-yl)-1-azabicyclo[3.3.1]non-3-ene oxalate from 4-chloro-3-(3-propoxy-1,2,5-thiadiazol-4-yl)-1-azabicyclo[3.3.1]non-3-ene. (Compound 97). M.p. 166°–167° C.
3-(3-Hexyloxy-1,2,5-thiadiazol-4-yl)-1-azabicyclo[3.3.1]non-3-ene oxalate from 4-chloro-3-(3-hexyloxy-1,2,5-thiadiazol-4-yl)-1-azabicyclo[3.3.1]non-3ene. (Compound 98). M.p. 100°–1 01° C.

EXAMPLE 48

3-(3-Isopentylthio-1,2,5-thiadiazol-4-yl)-1-azabicyclo[2.2.2]octane fumarate

A solution of 3-(3-chloro-1,2,5-thiadiazol-4-yl)-1-azabicyclo[2.2.2]octane (Compound 8) (420 mg, 1.83 mmol), sodiumhydrogen sulfide monohydrate (245 mg, 3.70 mmol) and potassium carbonate (780 mg, 5.64 mmol) in DMF (20 ml) was stirred at room temperature for 2 h. A solution of 1-bromo-3-methylbutane (420 mg, 2.75 mmol) in DMF (5 ml) was added, and the reaction mixture was stirred at room temperature for 3 h. Water (20 ml) was added and the mixture was extracted with ethyl acetate (3×100 ml). The combined extract was washed with brine, dried ($MgSO_4$), filtered and evaporated. The residue was purified by column chromatography (eluent: $CH_2Cl_2$.MeOH:$NH_4OH$ (8:2:0.5%)) to give the free base of the desired product in 400 mg yield. Crystallization of the residue with fumaric acid from isopropanol/ether gave the title compound in 370 mg yield. (Compound 99). M.p. 130°–132° C.

The following compounds were made as described above using the indicated alkylhalogenide instead of 1-bromo-3-methylbutane:
3-(3-(1-Methylpropylthio)-1,2,5-thiadiazol-4-yl)-1-azabicyclo[2.2.2]octane fumarate (Compound 100), using 2-bromobutane.
3-(3-Isobutylthio-1,2,5-thiadiazol-4-yl)-1-azabicyclo[2.2.2]octane fumarate (Compound 101 ), using 1-bromo-2-methylpropane.
3-(3-(2-Phenoxyethylthio)-1,2,5-thiadiazol-4-yl)-1-azabicyclo[2.2.2]octane fumarate (Compound 102), using β-bromophenetole. M.p. 135°–137° C.
3-(3-Cyanomethylthio-1,2,5-thiadiazol-4-yl)-1-azabicyclo[2.2.2]octane oxalate (Compound 103), using chloroacetonitrile. M.p. 188°–189° C.
3-(3-(3-(2-Thienyl)propylthio)-1,2,5-thiadiazol-4-yl)-1-azabicyclo[2.2.2]fumarate (Compound 104), using 1-chloro-3-(2-thienyl)propane. M.p. 134°–136° C.
3-(3-(4-Chlorobutylthio)-1,2,5-thiadiazol-4-yl)-1-azabicyclo[2.2.2]octane (Compound 105), using 1-bromo-4-chlorobutane.
3-(3-Methylthio-1,2,5-thiadiazol-4-yl)-1-azabicyclo[2.2.2]octane oxalate (Compound 131) using bromomethane. M.p. 185°–187° C.
3-(3-(2-(Phthalimido)Ethylthio)-1,2,5-thiadizol-4-yl)-1-azabicyclo[2.2.2]octane
3-(3-(2-Methoxyethylthio)-1,2,5-thiadiazol-4-yl)-1-azabicyclo[2.2.2]octane oxalate (Compound 136) using 2-methoxyethylbromide. M.p. 124°–125° C.
3-(3-(2-(1,3-Dioxolan-2-yl)ethylthio)-1,2,5-thiadiazol-4-yl)-1-azabicyclo[2.2.2]octane oxalate (Compound 137) using 2-(1,3-dioxolan-2-yl)ethylbromide. M.p. 151°–153° C.
3-(3-(4-Pyridylmethylthio)-1,2,5-thiadiazol-4-yl)-1-azabicyclo[2.2.2]octane oxalate (Compound 138) using 4-(chloromethyl)pyridine. M.p. 155°–157° C.
3-(3-Cyclopropylmethylthio-1,2,5-thiadiazol-4-yl)-1-azabicyclo[2.2.2]octane oxalate (Compound 139) using cyclopropylmethylbromide. M.p. 217°–218° C.
3-(4-Fluorobenzylthio-1,2,5-thiadiazol-4-yl)-1-azabicyclo[2.2.2]octane oxalate (Compound 140) using 4-fluorobenzylbromide.

EXAMPLE 49

3-(3-(1-Methyltetrazol-5-ylthio)butylthio-1,2,5-thiadiazol-4-yl)-1-azabicyclo[2.2.2]octane oxalate A solution of 3-(3-(4-chlorobutylthio)-1,2,5-thiadiazol-4-yl)-1-azabicyclo[2.2.2]octane (Compound 105) (3.0 g, 9.5 mmol), potassium carbonate (10 g, 72 mmol) and 1-methyl-5-mercaptotetrazole (5.0 g, 43 mmol) in DMF (50 ml) was stirred at room temperature for 3 days. 1N hydrochloric acid was added to the reaction and the mixture was extracted with ether. The ether phase was discharged. The reaction mixture was made basic with 4N sodium hydroxide and then extracted with ether (3×150 ml). The combined ether phases were dried ($MgSO_4$) and evaporated. The residue was crystallized with oxalic acid from acetone to give the title compound in 420 mg yield. (Compound 106). M.p. 78°–80° C.

The following compounds were made as described above using the indicated mercapto derivative instead of 1-methyl-5-mercaptotetrazole:

3-(3-(2-Methyl-1,3,4-thiadiazol-5-ylthio)butylthio-1,2,5-thiadiazol-4-yl)-1-azabicyclo[2.2.2]octane oxalate (Compound 107), using 2-mercapto-5-methyl-1,3,4-thiadiazole. M.p. 104°–105° C.

3-(3-(4-(2-Benzothiazolyl)thio)butylthio-1,2,5-thiadiazol-4-yl)-1-azabicyclo[2.2.2]octane oxalate (Compound 108), using 2-mercaptobenzothiazole. M.p. 51°–53° C.

EXAMPLE 50

3-(3-(4-Ethylbenzyloxy)-1,2,5-thiadiazol-4-yl)-1-azabicyclo[2.2.2]octane oxalate To a solution of 4-ethylbenzyl alcohol (1.63 g, 12 mmol) in dry THF (20 ml) was added sodium hydride (50% dispersion in mineral oil) (50 mg, 12 mmol) at 0° C. The reaction mixture was stirred for 1 h, then a solution of 3-(3-chloro-1,2,5-thiadiazol-4-yl)-1-azabicyclo[2.2.2]octane (920 mg, 4 mmol) in THF was added dropwise. The reaction mixture was stirred for 3 h. 1N hydrochloric acid was added to the reaction mixture and extracted with ether. The ether phase was discharged. The reaction mixture was made basic with 4N sodium hydroxide and extracted with ether (3×200 ml). The combined ether phases were dried and evaporated. The residue was purified by column chromatography (eluent: $CH_2Cl_2$: $MeOH$:$NH_4OH$ (8:2:0.5%)). Crystallization with oxalic acid from acetone gave the title compound in 180 mg yield. (Compound 109). M.p. 100°–102° C.

EXAMPLE 51

The following compound was made as described in example 50 using 3-(2-thienyl)-1-propanol instead of 4-ethylbenzyl alcohol:

3-(3-(3-(2-Thienyl)propoxy)-1,2,5-thiadiazol-4-yl)-1-azabicyclo[2.2.2]octane fumarate. (Compound 110). M.p. 117°–121° C.

EXAMPLE 52

(+)-Exo-6-(3-butylthio-1,2,5-thiadiazol-4-yl)-1-azabicyclo[3.2.1]octane (+) L-tartrate To a solution of (+) exo 6-(3-butylthio-1,2,5-thiadiazol-4-yl)-1-azabicyclo[3.2.1]octane (Compound 30) (28.3 g, 0.1 mol) in a 1:1 mixture of ethanol and ethyl acetate (2.165 l, 50 ml/g) (+) L-tartaric acid(15.0 g, 0.1 mol) was added, and the mixture heated until a clear solution was obtained. After cooling at 4° C. overnight, the precipitated crystals were filtered giving 19.5 g of crude material enriched with (−) exo 6-(3-butylthio-1,2,5-thiadiazol-4-yl)-1-azabicyclo[3.2.1]octane (+) L-tartrate. The mother liquor was evaporated at reduced pressure giving 23.8 g of crude material enriched with (+) exo 6-(3-butylthio-1,2,5-thiadiazol-4-yl)-1-azabicyclo[3.2.1]octane (+) L-tartrate. This material was dissolved in a 1:1 mixture of ethanol/ethyl acetate (1.19 l, 50 ml/g) and heated at reflux. After cooling at 4° C. overnight the precipitated crystals were filtered off. The mother liquor was evaporated and recrystallized from a ethanol/ethyl acetate mixture (50 ml/g). The title compound finally crystallized from the ethanol/ethyl acetate solvent mixture (50 ml/g) in 4.97 g yield. (Compound 111). M.p. 128°–129° C. $[\alpha]_D$=+28.9° (free base, MeOH).

EXAMPLE 53

(−)-Exo-6-(3-butylthio-1,2,5-thiadiazol-4-yl)-1-azabicyclo[3.2.1]octane (−) D-tartrate This compound was made in exactly the same manner as described in example 52 using (−) D-tartaric acid (Compound 112). M.p. 128°–130° C. $[\alpha]_D$=−27.5° (free base, MeOH).

EXAMPLE 54

(+)-Exo-6-(3-propylthio-1,2,5-thiadiazol-4-yl)-1-azabicyclo[3.2.1]octane (+) L-tartrate To a solution of (+)-exo-6-(3-propylthio-1,2,5-thiadiazol-4-yl)-1-azabicyclo[3.2.1]octane (Compound 58) (4.50 g, 17.6 mmol) in water/ethanol (20:80, 180 ml) was added (+) L-tartaric acid (2.64 g, 17.6 mmol). Ether (90 ml) was added and the mixture was cooled at 4° C. overnight. The precipitated crystals were collected by filtration. Recrystallization twice from ethanol/water/ether (10:40:50) gave the title compound in 1.5 g yield. (Compound 113). M.p. 163°–165° C. $[\alpha]_D$=+4.4° (free base, MeOH).

EXAMPLE 55

(−)-Exo-6-(3-propylthio-1,2,5-thiadiazol-4-yl)-1-azabicyclo[3.2.1]octane (−) D-tartrate This compound was made in exactly the same manner as described in example 54 using (−) D-tartaric acid. (Compound 114). M.p. 164°–165° C. $[\alpha]_D$=−4.2° (free base, MeOH).

EXAMPLE 56

Exo-6-(3-butylsulfonyl-1,2,5-thiadiazol-4-yl)-1-azabicyclo[3.2.1]octane oxalate

An acidic solution of exo 6-(3-butylthio-1,2,5-thiadiazol-4-yl)-1-azabicyclo-[3.2.1]octane (Compound 30) (2.5 g, 0.0088 mol) in $H_2O$ (20 ml+9 ml 1 N HCl) was cooled in an ice-water bath as oxone (8 g, 0.13 mol) in $H_2O$ (40 ml) was added dropwise. Cooling was removed and after stirring overnight the reaction was again cooled and the pH adjusted to 9. The mixture was extracted with $CHCl_3$ (3×30 ml), the extracts dried, and the solvent evaporated. The residue was suspended in EtOAc (100 ml) and extracted with saturated aqueous $K_2CO_3$ (15 ml), brine, the solvent dried and evaporated to give a yellow oil (2.6 g). The oxalate salt crystallized from EtOAc. M.p. 107°–108° C. (Compound 115).

Analysis $C_{13}H_{21}$,$N_3O_2S_2$-$C_2H_2O_4$, C,H,N; Theory C, 44.43; H, 5.72; N, 10.36 Found C, 44.67; H, 5.70; N, 10.38.

Exo-6-(3-(2,2,3,3,4,4,4-heptafluorobutyloxy)-1,2,5-thiadiazol-4-yl)-1-azabicyclo[3.2.1]octane oxalate A suspension of NaH (0.11 g 60% NaH in oil, 0.0028 mol) in THF (15 ml) was cooled to 11° C. as 2,2,3,3,4,4,4-heptafluorobutanol (0.56 g, 0.0074 mol) was added dropwise. After gas evolution ceased, a solution of the free base of (Compound 115) (0.8 g, 0.00254 mol) in THF (25 ml) was added and the reaction warmed to 35°–45° C. for 1.25 h subsequently stirred at ambient overnight and then heated to reflux for 4 h. Another solution of sodium heptafluorobutoxide (0.0028 mol) prepared as above was added and the solution was heated to reflux 1 h. The reaction was treated with H₂O (10 ml), diluted with ether, and extracted with 1 N HCl (2×10 ml). The acid extracts were made basic and extracted with EtOAc (3×25 ml). The organic extracts were dried, solvent evaporated and residue purified by radial chromatography (2.5% EtOH-0.25% NH₄OH-CHCl₃) to give a yellow oil (0.48 g). The oxalate salt crystallized from EtOAc to give a white solid. (Compound 116). M.p. 115°–116° C.

Analysis $C_{13}H_{14}F_7N_3OS \cdot C_2H_2O_4$, C,H,N; Theory C, 37.27; H, 3.34; N, 8.69; Found C, 37.55; H, 3.49; N, 8.80.

The following compounds were made in the same manner as described above using the indicated alcohol instead of 2,2,3,3,4,4,4-heptafluorobutanol:

Exo-6-(3-methoxy-1,2,5-thiadiazol-4-yl)-1-azabicyclo[3.2.1]octane oxalate, (Compound 117) using methanol. M.p. 143°–145° C.

Exo-6-(3-ethoxy-1,2,5-thiadiazol-4-yl)-1-azabicyclo[3.2.1]octane oxalate, (Compound 118) using ethanol. M.p. 90°–92° C.

Exo-6-(3-propoxy-1,2,5-thiadiazol-4-yl)-1-azabicyclo[3.2.1]octane oxalate, (Compound 119) using propanol. M.p. 152°–154° C.

Exo-6-(3-butoxy-1,2,5-thiadiazol-4-yl)-1-azabicyclo[3.2.1]octane oxalate, (Compound 120) using butanol.

Exo-6-(3-pentyloxy-1,2,5-thiadiazol-4-yl)-1-azabicyclo[3.2.1]octane oxalate, (Compound 121) using pentanol. M.p. 109°–110° C.

Exo-6-(3-hexyloxy-1,2,5-thiadiazol-4-yl)-1-azabicyclo[3.2.1]octane oxalate, (Compound 122) using hexanol. M.p. 109°–111° C.

Exo-6-(3-isohexyloxy-1,2,5-thiadiazol-4-yl)-1-azabicyclo[3.2.1]octane dioxalate, (Compound 123) using isohexanol. M.p. 94°–96° C.

Exo-6-(3-(2-butynyloxy)-1,2,5-thiadiazol-4-yl)-1-azabicyclo[3.2.1]octane oxalate, (Compound 124) using 2-butyn-1-ol. M.p. 119°–121° C.

EXAMPLE 57

Exo-6-(3-(3-(2-thienyl)-1-propylthio)-1,2,5-thiadiazol-4-yl)-1-azabicyclo[3.2.1]octane oxalate A solution of 6-(3-chloro-1,2,5-thiadiazol-4-yl)-1-azabicyclo[3.2.1]octane (mixture of exo- and endo-isomers (200 mg, 0.9 mmol)) in DMF (10 ml) was cooled to 5° C. whereupon potassium carbonate (180 mg, 1.3 mmol) and sodium hydrosulfide monohydrate (71 mg, 1.0 mmol) were added to the reaction. Stirred for 1 h then potassium carbonate (120 mg, 0.9 mmol) and a solution of 3-(2-thienyl)-1-chloropropane (154 mg, 1.0 mmol) in DMF (5 ml) were added to the reaction and stirred for 1 h at room temperature. The reaction was quenched with water then extracted with ethyl acetate (3×75 ml). The organic phase was dried over NaCl/Na₂SO₄ then evaporated. The residue was purified by radial chromatography eluting with 1% NH₄OH/10% EtOH in CHCl₃. The exo-isomer was isolated and the oxalate salt made to yield 29 mg of the title compound. (Compound 125). M.p. 157°–160° C.

The following compounds were made in exactly the same manner using the appropriate starting material:

Exo-6-(3-(4-fluorobenzylthio)-1,2,5-thiadiazol-4-yl)-1-azabicyclo[3.2.1]octane oxalate (Compound 141) using 4-fluorobenzylbromide. M.p. 152.5°–153.5° C.

Exo-6-(3-(4-chlorobenzylthio)-1,2,5-thiadiazol-4-yl)-1-azabicyclo[3.2.1]octane oxalate (Compound 142) using 4-chlorobenzylbromide. M.p. 168°–170° C.

Exo-6-(3-(4-methylbenzylthio)-1,2,5-thiadiazol-4-yl)-1-azabicyclo[3.2.1]octane oxalate (Compound 143) using 4-methylbenzylbromide. M.p. 176.5°–178° C.

Exo-6-(3-(4-trifluoromethoxybenzylthio)-1,2,5-thiadiazol-4-yl)-1-azabicyclo[3.2.1]octane oxalate (Compound 144) using 4-trifluoromethoxybenzylbromide. M.p. 175°–176.5° C.

Exo-6-(3-(4-thiocarbamylbenzylthio)-1,2,5-thiadiazol-4-yl)-1-azabicyclo[3.2.1]octane oxalate (Compound 145) using 4-thiocarbamylbenzylbromide. M.p. 125° C. dec.

Exo-6-(3-(4-methylsulfonylbenzylthio)-1,2,5-thiadiazol-4-yl)-1-azabicyclo[3.2.1]octane oxalate (Compound 146) using 4-methylsulfonylbenzylbromide. M.p. 125° C. dec.

Exo-6-(3-(5,5,5-trifluoropentylthio)-1,2,5-thiadiazol-4-yl)-1-azabicyclo[3.2.1]octane oxalate (Compound 147) using 5,5,5-trifluoropentylbromide. M.p. 125°–127° C.

Exo-6-(3-(3,3,3-trifluoropropylthio)-1,2,5-thiadiazol-4-yl)-1-azabicyclo[3.2.1]octane oxalate (Compound 148) using 3,3,3-trifluoropropylbromide. M.p. 93°–96° C.

Endo-6-(3-(3-(2-thienyl)-1-propylthio)-1,2,5-thiadiazol-4-yl)-1-azabicyclo[3.2.1]octane oxalate The endo-isomer was isolated from the above residue in the same manner as described for the exo-isomer. (Compound 126). M.p. 125°–128° C.

Endo-6-(3-(4,4,4-trifluorobutylthio)-1,2,5-thiadiazol-4-yl)-1-azabicyclo[3.2.1]octane oxalate (Compound 127) was made in the same manner as described above using 4,4,4-trifluoro-1-bromobutane instead of 3-(2-thienyl)-1-chloropropane. M.p. 75°–78° C.

Endo-6-(3-(6,6,6-trifluoro-1-hexylthio)-1,2,5-thiadiazol-4-yl)-1-azabicyclo[3.2.1]octane oxalate (Compound 128) was made as described above using 6,6,6-trifluoro-1-bromohexane instead of 3-(2-thienyl)-1-chloropropane. M.p. 130°–133° C.

Endo-6-(3-(4-trifluoromethoxybenzylthio)-1,2,5-thiadiazol-4-yl)-1-azabicyclo[3.2.1]octane oxalate (Compound 149) using 4-trifluoromethoxybenzylbromide. M.p. 150°–152.5° C.

Endo-6-(3-(4-methylbenzylthio)-1,2,5-thiadiazol-4-yl)-1-azabicyclo[3.2.1]octane oxalate (Compound 150) using 4-methylbenzylbromide. M.p. 158°–161° C.

Endo-6-(3-(4-fluorobenzylthio)-1,2,5-thiadiazol-4-yl)-1-azabicyclo[3.2.1]octane oxalate (Compound 151) using 4-fluorobenzylbromide. M.p. 146°–150° C.

Exo-6-(3-cyclopropylmethylthio-1,2,5-thiadiazol-4-yl)-1-azabicyclo[3.2.1]octane oxalate from cyclopropylmethylbromide. (Compound 175). M.p. 200°–201° C.

Exo-6-(3-(2-(1,3-dioxolane-2-yl)-ethylthio)-1,2,5-thiadiazol-4-yl)-1-azabicyclo[3.2.1]octane oxalate from 1-bromo-2-(dioxolanyl)ethane. (Compound 176). M.p. 147°–149° C.

Exo-6-(3-(4-methoxybenzylthio)-1,2,5-thiadiazol-4-yl)-1-azabicyclo[3.2.1]octane oxalate from 4-methoxybenzylchloride. (Compound 177). M.p. 170°–171° C.

Exo-6-(3-(2-methoxyethylthio)-1,2,5-thiadiazol-4-yl)-1-azabicyclo[3.2.1]octane oxalate from 1-bromo-2-methoxyethane. (Compound 178). M.p. 142°–144° C.

Exo-6-(3-(3-hydroxypropylthio)-1,2,5-thiadiazol-4-yl)-1-azabicyclo[3.2.1]octane oxalate from 1-bromo-3-hydroxypropane. (Compound 179). M.p. 115°–116° C.

Exo-6-(3-(4,4,4-trifluorobutylthio)-1,2,5-thiadiazol-4-yl)-1-azabicyclo[3.2.1]octane oxalate from 4,4,4-trifluoro-1-bromobutane. (Compound 180). M.p. 132°–134° C.

Endo-6-(3-cyclopropylmethylthio-1,2,5-thiadiazol-4-yl)-1-azabicyclo[3.2.1]octane oxalate from cyclopropylmethylbromide. (Compound 181). M.p. 152°–154° C.

Endo-6-(3-(4-methoxybenzylthio)-1,2,5-thiadiazol-4-yl)-1-azabicyclo[3.2.1]octane oxalate from 4-methoxybenzylchloride. (Compound 212). M.p. 155°–158° C.
Endo-6-(3-(2-methoxyethylthio)-1,2,5-thiadiazol-4-yl)-1-azabicyclo[3.2.1]octane oxalate from 1-bromo-2-methoxyethane. (Compound 182). M.p. 108°–112° C.
Endo-6-(3-(4-trifluoromethylbenzylthio)-1,2,5-thiadiazol-4-yl)-1-azabicyclo[3.2.1]octane oxalate from 4-trifluoromethylbenzylchloride. (Compound 183). M.p. 154°–156° C.
5-(3-(4-Cyanobenzylthio)-1,2,5-thiadiazol-4-yl)-1-azabicyclo[3.2.1]octane oxalate from 5-(3-chloro-1,2,5-thiadiazol-4-yl)-1-azabicyclo[3.2.1]octane and 4-cyanobenzylchloride. (Compound 172). M.p. 136°–138° C.

EXAMPLE 5

(+)-Exo-6-(3-butylsulfonyl-1,2,5-thiadiazol-4-yl)-1-azabicyclo[3.2.1]octane oxalate A solution of (+)-exo-6-(3-butylthio-1,2,5-thiadiazol-4-yl)-1-azabicyclo[3.2.1]octane tartrate (Compound 111) (4.4 g, 10.1 mmol) in water was treated with saturated aqueous $NaHCO_3$ until basic then extracted with ethyl acetate (3×100 ml). The organic phase was dried over $NaCl/Na_2SO_4$ then evaporated. The residue was taken up in 1N $HCl_{(aq)}$ and water (23 ml) and cooled to 0° C. A solution of oxone (9.2 g, 15.0 mmol) in water (45 ml) was added dropwise to the reaction then stirred overnight at room temperature. The pH of the reaction was adjusted to 9 then extracted with chloroform. The organic phase was dried over $NaCl/Na_2SO_4$ then evaporated to yield 3.9 g of free base. Crystallization with oxalic acid gave the title compound. (Compound 129). M.p. 147°–151° C.

The following compounds were made in exactly the same manner using the appropriate starting material:
(+)-Exo-(5R,6R)-6-(3-propylsulfonyl-1,2,5-thiadiazol-4-yl)-1-azabicyclo[3.2.1]octane oxalate (Compound 152) M.p. 160°–162° C.
(–)-Exo-(5S,6S)-6-(3-propylsulfonyl-1,2,5-thiadiazol-4-yl)-1-azabicyclo[3.2.1]octane oxalate (Compound 153) M.p. 160°–162° C.
Exo-6-(3-propylsulfonyl-1,2,5-thiadiazol-4-yl)-1-azabicyclo[3.2.1]octane oxalate. (Compound 184). M.p. 201°–203° C.

EXAMPLE 59

(+)-Exo-6-(3-(4,4,4-trifluoro-1-butylthio)-1,2,5-thiadiazol-4-yl)-1-azabicyclo[3.2.1]octane oxalate A solution of (+)-exo-6-(3-butylsulfonyl-1,2,5-thiadiazol-4-yl)-1-azabicyclo[3.2.1]octane (Compound 129) (1.3 g, 4.1 mmol) in DMF (20 ml) was warmed to 40° C. whereupon $Na_2S.9H_2O$ (1.2 g, 5.0 mmol) was added to the reaction. The reaction was heated to 100° C. for 3 h whereupon 1-bromo-4,4,4-trifluorobutane in DMF (5 ml) was added. Stirred at 100° C. for 1 h then at room temperature overnight. Poured the reaction into water then extracted with ethyl acetate (3×100 ml). The organic phase was dried over $NaCl/Na_2SO_4$ then evaporated. The residue was purified by radial chromatography eluting with 2% $NH_4OH$/20% EtOH in $CHCl_3$. The oxalate salt was made to yield 545 mg of the title compound (Compound 130). M.p. 147°–151° C.

EXAMPLE 60

3-(1,2,5-Thiadiazol-3-yl)-1-azabicyclo[2.2.2]octane fumarate

To a solution of 1-butanethiol (2.2 ml, 20 mmol) in THF (50 ml) was added sodium hydride (50% suspension in mineral oil, 960 mg, 20 mmol) at 0° C. The reaction was stirred for 1 h, whereafter a solution of 3-(3-chloro-1,2,5-thiadiazol-4-yl)-1-azabicyclo[2.2.2]octane (830 mg, 3.6 mmol) in THF (25 ml) was added. The reaction mixture was stirred at room temperature for 2 h. Water was added and the mixture extracted with ethyl acetate. The organic phase was dried and evaporated and the residue purified by column chromatography (eluent: $CH_2Cl_2$:MeOH:$NH_4OH$ (80:20:0.5)). Crystallization with fumaric acid from isopropanol/ether gave the title compound in 70 mg yield (Compound 132). M.p. 177°–179° C.

EXAMPLE 61

(–) 1-Azabicyclo[3.2.1]octan-6-one (+) camphorsulfonate

To a solution of (+) 1-azabicyclo[3.2.1]octan-6-one (124 g, 1 mol) in ethanol (100 ml) was added a solution of (+) camphorsulfonic acid (232 g, 1.0 mol) in 200 ml ethanol. The mixture was heated to 70° C. and slowly cooled over 2 hours to 5° C. The precipitated crystals were collected by filtration and washed with cold ethanol (3×40 ml). The crude compound was crystallized from ethanol (150 ml) giving the title compound in 57.3 g yield. M.p. 267°–268° C. (decomp.) $[\alpha]_D$=+48° (water).

EXAMPLE 62

(+) 1-Azabicyclo[3.2.1]octan-6-one (–) camphorsulfonate

This compound was made in exactly the same manner as described in example 1 using (+) 1-azabicyclo[3.2.1]octan-6-one and (–) camphorsulfonic acid. M.p. 267°–268° C. (decomp.) $[\alpha]_D$=–48° (water).

EXAMPLE 63

A. (–) Ethyl (1-azabicyclo[3.2.1]octan-6-ylidene)cyanoacetate hydrochloride (+) 1-Azabicyclo[3.2.1]octan-6-one (–) camphorsulfonate (61.8 g, 135.0 mmol) and triethylamine (20.4 g, 202 mmol) and ethyl cyanoacetate (61.8 g, 547 mmol) were mixed and stirred at room temperature for 6 days. Toluene (120 ml) and water (120 ml) were added to the reaction mixture and the pH was adjusted to 2 with concentrated hydrochloric acid. The phases were separated and the water phase extracted with toluene (30 ml). The combined organic phases were washed with water (20 ml). The combined water phases were adjusted to pH=9.4 with $NH_3$ (25% in water) and extracted with toluene (1×120 ml, 1×60 ml). The combined toluene extracts were evaporated. The residue was dissolved in ethanol (120 ml) and concentrated hydrochloric acid (16 ml) was added. The title compound precipitated in 22 g yield. Upon evaporation of the mother liquor and crystallization from ethanol (40 ml) further 14.6 g of the title compound was isolated.

B. Exo- and Endo-6-chloro-6-(3-chloro-1,2,5-thiadiazol-4-yl)-1-azabicyclo[3.2.1]octane (+) L-tartrate (–) Ethyl (1-azabicyclo[3.2.1]octan-6-ylidene)cyanoacetate (220 g, 1 mol) was dissolved in abs. ethanol (500 ml). Palladium on carbon (10 g, 5%) was added and the mixture treated with hydrogen in a Parr shaker at 20 psi for 10 hours. The catalyst was filtered off, and the solution evaporated to a final volume of 400 ml. This solution was added to a solution of sodium (25.3 g, 1.1 mol) in ethanol (200 ml). Isoamylnitrite (183.3 g, 1.56 mol) was added at 0°–5° C. The reaction mixture was warmed to room temperature and stirred at this temperature for 6 hours. The reaction mixture was cooled to 4° C. and left at 4° C. overnight. The reaction mixture was evaporated at reduced pressure, toluene (300 ml) was added and the mixture was again evaporated. The residue was dissolved in DMF (300 ml) and slowly added to a mixture of sulfurmonochloride (466 g, 3.5 mol) in DMF (140 ml) at 0°–5° C. The temperature was slowly raised to 20° C. over 3 hours and the reaction mixture was stirred at room temperature overnight. Water (750 ml) was carefully added. The pH was adjusted to 4 by addition of sodiumhydroxide solution (36% NaOH). The mixture was filtered at 70° C., cooled and basified with sodiumhydroxide. The water phase was extracted with toluene (900 ml+400 ml). The organic phases were evaporated. The residue was dissolved in ethanol (670 ml) and (+) L-tartaric acid (117 g, 0.8 mol) was added. The precipitated crystals were filtered giving the title compound in 270 g yield.

The following compounds were prepared in exactly the same manner:
2-Methyl-6-chloro-6-(3-chloro-1,2,5-thiadiazol-4-yl)-1-azabicyclo[3.2.1]octane starting from 2-methyl-1-azabicyclo[3.2.1]octan-6-one.

8-Methyl-6-chloro-6-(3-chloro-1,2,5-thiadiazol-4-yl)-1-azabicyclo[3.2.1]octane starting from 8-methyl-1-azabicyclo[3.2.1]octan-6-one.

C. Exo-6-(3-chloro-1,2,5-thiadiazol-4-yl)-1-azabicyclo[3.2.1]octane and endo-6-(3-chloro-1,2,5-thiadiazol-4-yl)-1-azabicyclo[3.2.1]octane hydrochloride 6-Chloro-6-(3-chloro-1,2,5-thiadiazol-4-yl)-1-azabicyclo[3.2.1]octane (121 g, 0.6 mol) dissolved in ethanol (1.5 l) was treated with Raney Nickel (20 ml, 50%) and hydrogen at atmospheric pressure. The catalyst was filtered and the ethanol evaporated at reduced pressure. The residue was recrystallized from ethanol (400 ml) giving the title compound in 115.8 g yield.

The following compounds were made in exactly the same manner:
Exo-2-methyl-6-(3-chloro-1,2,5-thiadiazol-4-yl)-1-azabicyclo[3.2.1]octane (Compound 169) and endo-2-methyl-6-(3-chloro-1,2,5-thiadiazol-4-yl)-1-azabicyclo[3.2.1]octane (Compound 170) starting from exo/endo-2-methyl-6-chloro-6-(3-chloro-1,2,5-thiadiazol-4-yl)-1-azabicyclo[3.2.1]octane.
Exo-8-methyl-6-(3-chloro-1,2,5-thiadiazol-4-yl)-1-azabicyclo[3.2.1]octane (Compound 171) and endo-8-methyl-6-(3-chloro-1,2,5-thiadiazol-4-yl)-1-azabicyclo[3.2.1]octane (Compound 171) starting from exo/endo-8-methyl-6-chloro-6-(3-chloro-1,2,5-thiadiazol-4-yl)-1-azabicyclo[3.2.1]octane.

D. (+)-Exo-6-(3-butylthio-1,2,5-thiadiazol-4-yl)-1-azabicyclo[3.2.1]octane (+) L-tartrate Starting from a mixture of exo- and endo-6-(3-chloro-1,2,5-thiadiazol-4-yl)-1-azabicyclo[3.2.1]octane described in example 63C, the chlorine was substituted with butylthio as described in example 14. A 1:9 mixture of exo- and endo-6-(3-butylthio-1,2,5-thiadiazol-4-yl)-1-azabicyclo[3.2.1]octane (10 g, 35 mmol) was dissolved in toluene (40 ml) and treated with potassium tert-butoxide (0.5 g) at reflux for 1 hour. The toluene solution was washed with water (15 ml) dried and evaporated. The residue crystallized with (+) L-tartaric acid giving the optical pure title compound in 12.5 g yield. (Compound 111 ). M.p. 128°–129° C.

EXAMPLE 64

Using resolved exo- and endo-6-(3-chloro-1,2,5-thiadiazol-4-yl)-1-azabicyclo[3.2.1]octane (example 63) obtained from resolved (−)-1-azabicyclo[3.2.1]-octan-6-one (example 61) or (+) 1-azabicyclo[3.2.1]octan-6-one (example 62) the following compounds were synthesized using the appropriate alkylhalogenide and separating exo- and endo compounds by column chromatography:
(+)-Exo-(5R,6R)-6-(3-(4-cyanobenzylthio)-1,2,5-thiadiazol-4-yl)-1-azabicyclo[3.2.1]octane oxalate (Compound 154) using 4-cyanobenzylbromide. M.p. 196°–197° C.
(−)-Exo-(5S,6S)-6-(3-(4-cyanobenzylthio)-1,2,5-thiadiazol-4-yl)-1-azabicyclo[3.2.1]octane oxalate (Compound 155) using 4-cyanobenzylbromide. M.p. 195°–196° C.
(−)-Endo-6-(3-propylthio-1,2,5-thiadiazol-4-yl)-1-azabicyclo[3.2.1]octane (+) L-tartrate (Compound 156) using propylbromide.
(+)-Exo-(5R,6R)-6-(3-isohexylthio-1,2,5-thiadiazol-4-yl)-1-azabicyclo[3.2.1]octane (+) L-tartrate (Compound 157) using isohexylbromide. M.p. 152°–153° C.
(−)-Exo-6-(3-isohexylthio-1,2,5-thiadiazol-4-yl)-1-azabicyclo[3.2.1]octane oxalate (Compound 158) using isohexylbromide. M.p. 118°–122° C.
(+)-Endo-6-(3-isohexylthio-1,2,5-thiadiazol-4-yl)-1-azabicyclo[3.2.1]octane (+) L-tartrate (Compound 159) using isohexylbromide. M.p. 102°–103° C.
(−)-Endo-(5S,6R )-6-(3-(4,4,4-trifluorobutylthio)-1,2,5-thiadiazol-4-yl)-1-azabicyclo[3.2.1]octane (−) D-tartrate (Compound 160) using 4,4,4-trifluorobutylbromide. M.p. 94°–96° C.
(+)-Endo-(5R,6S )-6-(3-(4,4,4-trifluorobutylthio)-1,2,5-thiadiazol-4-yl)-1-azabicyclo[3.2.1]octane (+) L-tartrate (Compound 161) using 4,4,4-trifluorobutylbromide. M.p. 94°–96° C.
(−)-Endo-(5S,6R)-6-(3-(4-cyanobenzylthio)-1,2,5-thiadiazol-4-yl)-1-azabicyclo[3.2.1]octane oxalate (Compound 162) using 4-cyanobenzylbromide. M.p. 167°–172° C.
(+) -Endo-(5R,6S )-6-(3-(4-cyanobenzylthio)-1,2,5-thiadiazol-4-yl)-1-azabicyclo[3.2.1]octane oxalate (Compound 163) using 4-cyanobenzylbromide. M.p. 168°–172° C.
(+)-Endo-6-(3-propylthio-1,2,5-thiadiazol-4-yl)-1-azabicyclo[3.2.1]octane oxalate (Compound 164) using propylbromide. M.p. 64°–65° C.
(+) -Exo-6-(3-(3,3,3-trifluoropropylthio)-1,2,5-thiadiazol-4-yl)-1-azabicyclo[3.2.1]octane hydrochloride (Compound 165) using 3,3,3-trifluoropropylbromide. M.p. 199°–202° C.
(+)-Exo-6-(3-(3-(2-thienyl)propylthio)-1,2,5-thiadiazol-4-yl)-1-azabicyclo[3.2.1]octane oxalate (Compound 166) using 3-(2-thienyl)propylchloride. M.p. 135°–139° C.
(−)-Exo-6-(3-(4,4,4-trifluorobutylthio)-1,2,5-thiadiazol-4-yl)-1-azabicyclo[3.2.1]octan oxalate (Compound 167) using 4,4,4-trifluorobutylbromide. M.p. 153°–154° C.
(+)-Endo-6-(3-(3,3,3-trifluoropropylthio)-1,2,5-thiadiazol-4-yl)-1-azabicyclo-[3.2.1]octane hydrochloride (Compound 168) using 3,3,3-trifluoropropylbromide. M.p. 170°–174° C.
(+)-Exo-6-(3-methylthio-1,2,5-thiadiazol-4-yl)-1-azabicyclo[3.2.1]octane oxalate. (Compound 185). M.p. 144°–145° C.
(+)-Exo-6-(3-ethylthio-1,2,5-thiadiazol-4-yl)-1-azabicyclo[3.2.1]octane oxalate. (Compound 186). M.p. 120°–124° C.

(+)-Exo-6-(3-pentylthio-1,2,5-thiadiazol-4-yl)-1-azabicyclo[3.2.1]octane oxalate. (Compound 187). M.p. 128°–129° C.
(+)-Exo-6-(3-hexylthio-1,2,5-thiadiazol-4-yl)-1-azabicyclo[3.2.1]octane oxalate. (Compound 188). M.p. 149°–150° C.
(−)-Exo-6-(3-methylthio-1,2,5-thiadiazol-4-yl)-1-azabicyclo[3.2.1]octane oxalate. (Compound 189). M.p. 144°–145° C.
(−)-Exo-6-(3-ethylthio-1,2,5-thiadiazol-4-yl)-1-azabicyclo[3.2.1]octane oxalate. (Compound 190). M.p. 120°–123° C.
(−)-Exo-6-(3-pentylthio-1,2,5-thiadiazol-4-yl)-1-azabicyclo[3.2.1]octane oxalate. (Compound 191). M.p. 132°–134° C.
(−)-Exo-6-(3-hexylthio-1,2,5-thiadiazol-4-yl)-1-azabicyclo[3.2.1]octane oxalate. (Compound 192). M.p. 149°–150° C.
(+)-Endo-6-(3-methylthio-1,2,5-thiadiazol-4-yl)-1-azabicyclo[3.2.1]octane oxalate. (Compound 193). M.p. 138°–139° C.
(+)-Endo-6-(3-ethylthio-1,2,5-thiadiazol-4-yl)-1-azabicyclo[3.2.1]octane oxalate. (Compound 194). M.p. 87°–89° C.
(+)-Endo-6-(3-pentylthio-1,2,5-thiadiazol-4-yl)-1-azabicyclo[3.2.1]octane oxalate. (Compound 195). M.p. 65°–70° C.
(+)-Endo-6-(3-hexylthio-1,2,5-thiadiazol-4-yl)-1-azabicyclo[3.2.1]octane oxalate. (Compound 196). M.p. 89°–90° C.
(−)-Endo-6-(3-methylthio-1,2,5-thiadiazol-4-yl)-1-azabicyclo[3.2.1]octane oxalate. (Compound 197). M.p. 137°–140° C.
(−)-Endo-6-(3-ethylthio-1,2,5-thiadiazol-4-yl)-1-azabicyclo[3.2.1]octane oxalate. (Compound 198). M.p. 107°–110° C.
(−)-Endo-6-(3-pentylthio-1,2,5-thiadiazol-4-yl)-1-azabicyclo[3.2.1]octane oxalate. (Compound 199). M.p. 85°–90° C.
(−)-Endo-6-(3-hexylthio-1,2,5-thiadiazol-4-yl)-1-azabicyclo[3.2.1]octane oxalate. (Compound 200). M.p. 132°–134° C.
(+)-Exo-6-(3-(4-trifluoromethylbenzylthio)-1,2,5-thiadiazol-4-yl)-1-azabicyclo[3.2.1]octane oxalate from 4-trifluoromethylbenzylchloride. (Compound 201). M.p. 172°–174° C.
(+)-Exo-6-(3-(4-nitrobenzylthio)-1,2,5-thiadiazol-4-yl)-1-azabicyclo[3.2.1]-octane oxalate from 4-nitrobenzylchloride. (Compound 202). M.p. 173°–174° C.
(+)-Exo-6-(3-(2-hydroxyethylthio)-1,2,5-thiadiazol-4-yl)-1-azabicyclo[3.2.1]octane oxalate from 2-hydroxy-1-chloroethane. (Compound 203). M.p. 179°–181° C.

In the above examples optical rotation is measured on the free base.

EXAMPLE 65

The following compounds were prepared in exactly the same manner as described in example 64:
Endo-2-methyl-6-(3-propylthio-1,2,5-thiadiazol-4-yl)-1-azabicyclo[3.2.1]octane oxalate from endo-2-methyl-6-(3-chloro-1,2,5-thiadiazol-4-yl)-1-azabicyclo[3.2.1]octane. (Compound 204). M.p. 123°–124° C.
Endo-8-methyl-6-(3-propylthio-1,2,5-thiadiazol-4-yl)-1-azabicyclo[3.2.1]octane oxalate from endo-8-methyl-6-(3-chloro-1,2,5-thiadiazol-4-yl)-1-azabicyclo[3.2.1]octane. (Compound 205). M.p. 172°–175° C.
Exo-2-methyl-6-(3-propylthio-1,2,5-thiadiazol-4-yl)-1-azabicyclo[3.2.1]octane oxalate from exo-2-methyl-6-(3-chloro-1,2,5-thiadiazol-4-yl)-1-azabicyclo[3.2.1]octane. (Compound 206). M.p. 155°–156° C.
Exo-8-methyl-6-(3-propylthio-1,2,5-thiadiazol-4-yl)-1-azabicyclo[3.2.1]octane oxalate from exo-8-methyl-6-(3-chloro-1,2,5-thiadiazol-4-yl)-1-azabicyclo[3.2.1]octane. (Compound 207). M.p. 144°–146° C.
Exo-2-methyl-6-(3-butylthio-1,2,5-thiadiazol-4-yl)-1-azabicyclo[3.2.1]octane oxalate from exo-2-methyl-6-(3-chloro-1,2,5-thiadiazol-4-yl)-1-azabicyclo[3.2.1]octane. (Compound 208). M.p. 160°–164° C.
Exo-8-methyl-6-(3-butylthio-1,2,5-thiadiazol-4-yl)-1-azabicyclo[3.2.1]octane oxalate from exo-8-methyl-6-(3-chloro-1,2,5-thiadiazol-4-yl)-1-azabicyclo[3.2.1]octane. (Compound 209). M.p. 143°–147° C.
Exo-2-methyl-6-(3-hexylthio-1,2,5-thiadiazol-4-yl)-1-azabicyclo[3.2.1]octane oxalate from exo-2-methyl-6-(3-chloro-1,2,5-thiadiazol-4-yl)-1-azabicyclo[3.2.1]octane. (Compound 210). M.p. 128°–131° C.
Exo-8-methyl-6-(3-hexylthio-1,2,5-thiadiazol-4-yl)-1-azabicyclo[3.2.1]octane oxalate from exo-8-methyl-6-(3-chloro-1,2,5-thiadiazol-4-yl)-1-azabicyclo[3.2.1]octane. (Compound 211). M.p. 140°–142° C.

We claim:
1. A compound of formula I

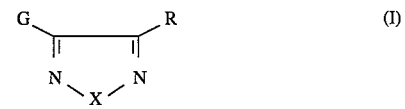

wherein

X is oxygen or sulphur;

R is hydrogen, amino, halogen, —CHO, —NO$_2$, —OR$^4$, —SR$^4$, —SOR$^4$, SO$_2$R$^4$, C$_{3-7}$-cycloalkyl, C$_{4-8}$-(cycloalkylalkyl, —Z—C$_{3-7}$-cycloalkyl or —Z—C$_{4-8}$-(cycloalkylalkyl) wherein R$^4$ is straight or branched C$_{1-15}$-alkyl, straight or branched C$_{2-15}$-alkenyl, straight or branched C$_{2-15}$-alkynyl, each of which is optionally substituted with one or more halogen(s), —CF$_3$, —CN, —OH, phenyl or phenoxy wherein the phenyl or phenoxy is optionally substituted with halogen, —CF$_3$, —CN, C$_{1-4}$-alkyl, C$_{1-4}$-alkoxy, —OCF$_3$, —CONH$_2$ or —CSNH$_2$; or R is phenyl or benzyloxycarbonyl, each of which is optionally substituted with halogen, —CN, C$_{1-4}$-alkyl, C$_{1-4}$-alkoxy, —OCF$_3$, —CONH$_2$ or —CSNH$_2$; or R is —OR$^5$Y, —SR$^5$Y, —OR$^5$ZY, —SR$^5$ZY, —O—R$^4$—Z—R$^5$ or —S—R$^4$—Z—R$^5$ wherein Z is oxygen or sulphur, R$^5$ is straight or branched C$_{1-5}$-alkyl, straight or branched C$_{2-15}$-alkenyl, straight or branched C$_{2-15}$-alkynyl, and Y is a heterocyclic group selected from the group consisting of thienyl, tetrazolyl, thiazolyl, thiadiazolyl, benzothiazolyl, phthalimido, pyridyl and 1,3-dioxolanyl wherein the heterocyclic group is optionally substituted at a carbon or nitrogen atom with straight or branched C$_{1-5}$-alkyl, phenyl or benzyl; and G is an azabicyclic ring of formula II

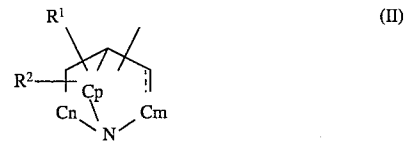

wherein the thiadiazole or oxadiazole ring is attached at any carbon atom of the azabicyclic ring;

R$^1$ and R$^2$ may be present at any appropriate position and independently are hydrogen, straight or branched C$_{1-5}$-alkyl, straight or branched C$_{2-5}$-alkenyl, straight or branched C$_{2-5}$-alkynyl, straight or branched C$_{1-10}$-alkoxy, —OH, halogen, —NH$_2$, carboxy or straight or branched C$_{1-5}$-alkyl substituted with —OH; m is 1, n is 2 and p is 1; and --- is a single or double bond; or a pharmaceutically acceptable salt thereof.

2. The compound according to claim 1, wherein R is —OR$^5$Y, —SR$^5$Y, —OR$^5$ZY, —SR$^5$ZY, —O—R$^4$—Z—R$^5$ or —S—R$^4$—Z—R$^5$ wherein Z is oxygen or sulphur, R$^5$ is straight or branched C$_{1-15}$-alkyl, straight or branched C$_{2-15}$-alkenyl, straight or branched C$_{2-15}$-alkynyl, and Y is a heterocyclic group selected from the group consisting of phthalimido, pyridyl and 1,3-dioxolanyl wherein the heterocyclic group is optionally substituted at a carbon or nitrogen atom with straight or branched C$_{1-6}$-alkyl, phenyl or benzyl.

3. The compound according to claim 1, wherein R is hydrogen, amino, —OR$^4$, —SR$^4$, —SOR$^4$, or —SO$_2$R$^4$, wherein R$^4$ is straight or branched C$_{1-15}$-alkyl, straight or branched C$_{2-15}$-alkenyl, straight or branched C$_{2-15}$-alkynyl, each of which is substituted with one or more phenyl or phenoxy wherein the phenyl or phenoxy is substituted with CF$_3$, —OCF$_3$, —CONH$_2$ or —CSNH$_2$; or R is phenyl or benzyloxycarbonyl, each of which is substituted with —OCF$_3$, —CONH$_2$ or —CSNH$_2$.

4. The compound according to claim 2, wherein X is sulfur.

5. The compound according to claim 4, wherein R$^1$ and R$^2$ are hydrogen.

6. The compound according to claim 4, wherein R is —SR$^4$, wherein R$^4$ is C$_{3-15}$-alkyl.

7. The compound according to claim 5, wherein R is —SR$^4$, wherein R$^4$ is C$_{2-15}$-alkenyl.

8. The compound according to claim 6, wherein R is —OR$^4$, wherein R$^4$ is C$_{3-15}$-alkyl.

9. The compound according to claim 6, wherein R is —OR$^4$, wherein R$^4$ is C$_{2-15}$-alkenyl.

10. The compound according to claim 1, wherein R is —CHO, —NO$_2$, —OR$^4$, —SR$^4$, —SOR$^4$, or —SO$_2$R$^4$, wherein R$^4$ is straight or branched C$_{3-15}$-alkyl, straight or branched C$_{2-15}$-alkenyl, straight or branched C$_{2-15}$-alkynyl, C$_{1-15}$-alkyl which is substituted with a phenyl group, wherein the phenyl group is optionally substituted with halogen, —CN, C$_{1-4}$-alkyl, or C$_{1-4}$-alkoxy; or R is phenyl or benzyloxycarbonyl, each of which is optionally substituted with halogen, —CN, C$_{1-4}$-alkyl, or C$_{1-4}$-alkoxy.

11. The compound according to claim 10, wherein X is sulfur.

12. The compound according to claim 11, wherein R$^1$ and R$^2$ are hydrogen.

13. The compound according to claim 11, wherein R is —SR$^4$, wherein R$^4$ is C$_{3-15}$-alkyl.

14. The compound according to claim 11, wherein R is —SR$^4$, wherein R$^4$ is C$_{2-15}$-alkenyl.

15. The compound according to claim 11, wherein R is —OR$^4$, wherein R$^4$ is C$_{3-15}$-alkyl.

16. The compound according to claim 11, wherein R is —OR$^4$, wherein R$^4$ is C$_{2-15}$-alkenyl.

17. The compound according to claim 1 selected from the following:

Endo-6-(3-hexylthio-1,2,5-thiadiazol-4-yl)-1-azabicyclo[3.2.1]octane;

Endo-6-(3-(5-hexenylthio)-1,2,5-thiadiazol-4-yl)-1-azabicyclo[3.2.1]octane;

Endo-6-(3-butylthio-1,2,5-thiadiazol-4-yl)-1-azabicyclo[3.2.1]octane;

Endo-6-(3-ethylthio-1,2,5-thiadiazol-4-yl)-1-azabicyclo[3.2.1]octane;

Endo-6-(3-pentylthio-1,2,5-thiadiazol-4-yl)-1-azabicyclo[3.2.1]octane;

Exo-6-(3-hexylthio-1,2,5-thiadiazol-4-yl)-1-azabicyclo[3.2.1]octane;

Exo-6-(3-butylthio-1,2,5-thiadiazol-4-yl)-1-azabicyclo[3.2.1]octane;

Exo-6-(3-pentylthio-1,2,5-thiadiazol-4-yl)-1-azabicyclo[3.2.1]octane;

Exo-6-(3-ethylthio-1,2,5-thiadiazol-4-yl)-1-azabicyclo[3.2.1]octane;

Endo-6-(3-propylthio-1,2,5-thiadiazol-4-yl)-1-azabicyclo[3.2.1]octane;

Exo-6-(3-propylthio-1,2,5-thiadiazol-4-yl)-1-azabicyclo[3.2.1]octane;

5-(3-Hexylthio-1,2,5-thiadiazol-4-yl)-1-azabicyclo[3.2.1]octane; or a pharmaceutically acceptable salt thereof.

18. The compound according to claim 1 selected from the following:

Exo-6-(3-chloro-1,2,5-thiadiazol-4-yl)-1-azabicyclo[3.2.1]octane;

Endo-6-(3-chloro-1,2,5-thiadiazol-4-yl)-1-azabicyclo[3.2.1]octane;

3-Chloro-2-(3-chloro-1,2,5-thiadiazol-4-yl)-8-azabicyclo[3.2.1]oct-2-ene;

5-(3-Chloro-1,2,5-thiadiazol-4-yl)-1-azabicyclo[3.2.1]octane; or a pharmaceutically acceptable salt thereof.

19. The compound according to claim 1 selected from the following:

Endo-6-(3-(3-phenylpropylthio)-1,2,5-thiadiazol-4-yl)-1-azabicyclo[3.2.1]octane;

Endo-6-(3-(4-cyanobenzylthio)-1,2,5-thiadiazol-4-yl)-1-azabicyclo[3.2.1]octane;

or a pharmaceutically acceptable salt thereof.

20. The compound according to claim 1 selected from the following:

Exo-6-(3-ethoxy-1,2,5-thiadiazol-4-yl)-1-azabicyclo[3.2.1]octane;

Endo-6-(3-ethoxy-1,2,5-thiadiazol-4-yl)-1-azabicyclo[3.2.1]octane;

Exo-6-(3-pentyloxy-1,2,5-thiadiazol-4-yl)-1-azabicyclo[3.2.1]octane;

Endo-6-(3-pentyloxy-1,2,5-thiadiazol-4-yl)-1-azabicyclo[3.2.1]octane; or a pharmaceutically acceptable salt thereof.

21. The compound according to claim 1 selected from the following:

(−)-Exo-6-(3-butylthio-1,2,5-thiadiazol-4-yl)-1-azabicyclo[3.2.1]octane;

(+)-Exo-6-(3-propylthio-1,2,5-thiadiazol-4-yl)-1-azabicyclo[3.2.1]octane;

(−)-Exo-6-(3-propylthio-1,2,5-thiadiazol-4-yl)-1-azabicyclo[3.2.1]octane;

Exo-6-(3-methylthio-1,2,5-thiadiazol-4-yl)-1-azabicyclo[3.2.1]octane;

Exo-6-(3-heptylthio-1,2,5-thiadiazol-4-yl)-1-azabicyclo[3.2.1]octane;

Exo-6-(3-isohexylthio-1,2,5-thiadiazol-4-yl)-1-azabicyclo[3.2.1]octane;

Exo-6-(3-isopentylthio-1,2,5-thiadiazol-4-yl)-1-azabicyclo[3.2.1]octane;

Endo-6-(3-methylthio-1,2,5-thiadiazol-4-yl)-1-azabicyclo[3.2.1]octane;

Endo-6-(3-isopentylthio-1,2,5-thiadiazol-4-yl)-1-azabicyclo[3.2.1]octane;

Endo-6-(3-isohexylthio-1,2,5-thiadiazol-4-yl)-1-azabicyclo[3.2.1]octane;

(+)-Exo-6-(3-butylthio-1,2,5-thiadiazol-4-yl)-1-azabicyclo[3.2.1]octane; or a pharmaceutically acceptable salt thereof.

22. The compound according to claim 1 selected from the following:

Endo-6-(3-(4,4,4-trifluorobutylthio)-1,2,5-thiadiazol-4-yl)-1-azabicyclo[3.2.1]octane;

Endo-6-(3-(6,6,6-trifluoro-1-hexylthio)-1,2,5-thiadiazol-4-yl)-1-azabicyclo[3.2.1]octane;

(+)-Exo-6-(3-(4,4,4-trifluoro-1-butylthio)-1,2,5-thiadiazol-4-yl)-1-azabicyclo[3.2.1]octane; or a pharmaceutically acceptable salt thereof.

23. The compound according to claim 1 selected from the following:

Exo-6-(3-(4-cyanobutylthio)-1,2,5-thiadiazol-4-yl)-1-azabicyclo[3.2.1]octane;

Exo-6-(3-cyanomethylthio-1,2,5-thiadiazol-4-yl)-1-azabicyclo[3.2.1]octane;

Exo-6-(3-(2-cyanoethylthio)-1,2,5-thiadiazol-4-yl)-1-azabicyclo[3.2.1]octane;

Exo-6-(3-(3-cyanopropylthio)-1,2,5-thiadiazol-4-yl)-1-azabicyclo[3.2.1]octane;

Endo-6-(3-cyanomethylthio-1,2,5-thiadiazol-4-yl)-1-azabicyclo[3.2.1]octane;

Endo-6-(3-(2-cyanoethylthio)-1,2,5-thiadiazol-4-yl)-1-azabicyclo[3.2.1]octane;

Endo-6-(3-(3-cyanopropylthio)-1,2,5-thiadiazol-4-yl)-1-azabicyclo[3.2.1]octane;

Endo-6-(3-(4-cyanobutylthio)-1,2,5-thiadiazol-4-yl)-1-azabicyclo[3.2.1]octane;

or a pharmaceutically acceptable salt thereof.

24. The compound according to claim 1 selected from the following:

Exo-6-(3-(4-cyanobenzylthio)-1,2,5-thiadiazol-4-yl)-1-azabicyclo[3.2.1]octane;

Exo-6-(3-(3-phenylpropylthio)-1,2,5-thiadiazol-4-yl)-1-azabicyclo[3.2.1]octane;

Exo-6-(3-(2-phenoxyethylthio )-1,2,5-thiadiazol-4-yl)-1-azabicyclo[3.2.1]octane;

Exo-6-(3-benzylthio-1,2,5-thiadiazol-4-yl)-1-azabicyclo[3.2.1]octane;

Endo-6-(3-(2-phenoxyethylthio)-1,2,5-thiadiazol-4-yl)-1-azabicyclo[3.2.1]octane;

Endo-6-(3-benzylthio-1,2,5-thiadiazol-4-yl)-1-azabicyclo[3.2.1]octane; or a pharmaceutically acceptable salt thereof.

25. The compound according to claim 1 selected from the following:

Exo-6-(3-butylsulfonyl-1,2,5-thiadiazol-4-yl)-1-azabicyclo[3.2.1]octane;

Exo-6-(3-(3-(2-thienyl)-1-propylthio)-1,2,5-thiadiazol-4-yl)-1-azabicyclo[3.2.1]octane;

Endo-6-(3-(3-(2-thienyl)-1-propylthio)-1,2,5-thiadiazol-4-yl)-1-azabicyclo[3.2.1]octane;

(+)-Exo-6-(3-butylsulfonyl-1,2,5-thiadiazol-4-yl)-1-azabicyclo[3.2.1]octane; or a pharmaceutically acceptable salt thereof.

26. The compound according to claim 1 which is:

Exo-6-(3-(2,2,3,3,4,4,4-heptafluorobutyloxy)-1,2,5-thiadiazol-4-yl)-1-azabicyclo[3.2.1]octane;

Exo-6-(3-methoxy-1,2,5-thiadiazol-4-yl)-1-azabicyclo[3.2.1]octane;

Exo-6-(3-ethoxy-1,2,5-thiadiazol-4-yl)-1-azabicyclo[3.2.1]octane;

Exo-6-(3-propoxy-1,2,5-thiadiazol-4-yl)-1-azabicyclo[3.2.1]octane;

Exo-6-(3-butoxy-1,2,5-thiadiazol-4-yl)-1-azabicyclo[3.2.1]octane;

Exo-6-(3-pentyloxy-1,2,5-thiadiazol-4-yl)-1-azabicyclo[3.2.1]octane;

Exo-6-(3-hexyloxy-1,2,5-thiadiazol-4-yl)-1-azabicyclo[3.2.1]octane;

Exo-6-(3-isohexyloxy-1,2,5-thiadiazol-4-yl)-1-azabicyclo[3.2.1]octane;

Exo-6-(3-(2-butynyloxy)-1,2,5-thiadiazol-4-yl)-1-azabicyclo[3.2.1]octane; or a pharmaceutically acceptable salt thereof.

27. The compound according to claim 1 which is:

Exo-6-(3-(4-fluorobenzylthio)-1,2,5-thiadiazol-4-yl)-1-azabicyclo[3.2.1]octane;

Exo-6-(3-(4-chlorobenzylthio)-1,2,5-thiadiazol-4-yl)-1-azabicyclo[3.2.1]octane;

Endo-6-(3-(4-fluorobenzylthio)-1,2,5-thiadiazol-4-yl)-1-azabicyclo[3.2.1]octane;

or a pharmaceutically acceptable salt thereof.

28. The compound according to claim 1 which is:

Exo-6-(3-(4-methylbenzylthio)-1,2,5-thiadiazol-4-yl)-1-azabicyclo[3.2.1]octane;

Endo-6-(3-(4-methylbenzylthio)-1,2,5-thiadiazol-4-yl)-1-azabicyclo[3.2.1]octane;

Endo-6-(3-(4-trifluoromethylbenzylthio)-1,2,5-thiadiazol-4-yl)-1-azabicyclo[3.2.1]octane;

(+)-Exo-6-(3-(4-trifluoromethylbenzylthio)-1,2,5-thiadiazol-4-yl)-1-azabicyclo[3.2.1]octane; or a pharmaceutically acceptable salt thereof.

29. The compound according to claim 1 which is:

Exo-6-(3-(4-trifluoromethoxybenzylthio)-1,2,5-thiadiazol-4-yl)-1-azabicyclo[3.2.1]octane;

Endo-6-(3-(4-trifluoromethoxybenzylthio)-1,2,5-thiadiazol-4-yl)-1-azabicyclo[3.2.1]octane;

Exo-6-(3-(4-methoxybenzylthio)-1,2,5-thiadiazol-4-yl)-1-azabicyclo[3.2.1]octane;

Endo-6-(3-(4-methoxybenzylthio)-1,2,5-thiadiazol-4-yl)-1-azabicyclo[3.2.1]octane; or a pharmaceutically acceptable salt thereof.

30. The compound according to claim 1 which is:

Exo-6-(3-(4-thiocarbamylbenzylthio)-1,2,5-thiadiazol-4-yl)-1-azabicyclo[3.2.1]octane;

Exo-6-(3-(4-methylsulfonylbenzylthio)-1,2,5-thiadiazol-4-yl)-1-azabicyclo[3.2.1]octane;

(+)-Exo-6-(3-(4-nitrobenzylthio)-1,2,5-thiadiazol-4-yl)-1-azabicyclo[3.2.1]octane; or a pharmaceutically acceptable salt thereof.

31. The compound according to claim 1 which is:

(+)-Exo-(5R,6R)-6-(3-(4-cyanobenzylthio)-1,2,5-thiadiazol-4-yl)-1-azabicyclo[3.2.1]octane;

(−)-Exo-(5S,6S)-6-(3-(4-cyanobenzylthio)-1,2,5-thiadiazol-4-yl)-1-azabicyclo[3.2.1]octane;

(−)-Endo-(5S,6R)-6-(3-(4-cyanobenzylthio)-1,2,5-thiadiazol-4-yl)-1-azabicyclo[3.2.1]octane;

(+)-Endo-(5R,6S)-6-(3-(4-cyanobenzylthio)-1,2,5-thiadiazol-4-yl)-1-azabicyclo[3.2.1]octane;

5-(3-(4-Cyanobenzylthio)-1,2,5-thiadiazol-4-yl)-1-azabicyclo[3.2.1]octane; or a pharmaceutically acceptable salt thereof.

32. The compound according to claim 1 which is:

Exo-6-(3-(5,5,5-trifluoropentylthio)-1,2,5-thiadiazol-4-yl)-1-azabicyclo[3.2.1]octane;

Exo-6-(3-(3,3,3-trifluoropropylthio)-1,2,5-thiadiazol-4-yl)-1-azabicyclo[3.2.1]octane;
(−)-Endo-(5S,6R)-6-(3-(4,4,4-trifluorobutylthio)-1,2,5-thiadiazol-4-yl)-1-azabicyclo[3.2.1]octane;
(+)-Endo-(5R,6S)-6-(3-(4,4,4-trifluorobutylthio)-1,2,5-thiadiazol-4-yl)-1-azabicyclo[3.2.1]octane;
(+)-Exo-6-(3-(3,3,3-trifluoropropylthio)-1,2,5-thiadiazol-4-yl)-1-azabicyclo[3.2.1]octane;
(−)-Exo-6-(3-(4,4,4-trifluorobutylthio)-1,2,5-thiadiazol-4-yl)-1-azabicyclo[3.2.1]octane;
(+)-Endo-6-(3-(3,3,3-trifluoropropylthio)-1,2,5-thiadiazol-4-yl)-1-azabicyclo[3.2.1]octane;
Exo-6-(3-(4,4,4-trifluorobutylthio)-1,2,5-thiadiazol-4-yl)-1-azabicyclo[3.2.1]octane; or
a pharmaceutically acceptable salt thereof.

33. The compound according to claim 1 which is:
Endo-2-methyl-6-(3-propylthio-1,2,5-thiadiazol-4-yl)-1-azabicyclo[3.2.1]octane;
Endo-8-methyl-6-(3-propylthio-1,2,5-thiadiazol-4-yl)-1-azabicyclo[3.2.1]octane;
Exo-2-methyl-6-(3-propylthio-1,2,5-thiadiazol-4-yl)-1-azabicyclo[3.2.1]octane;
Exo-8-methyl-6-(3-propylthio-1,2,5-thiadiazol-4-yl)-1-azabicyclo[3.2.1]octane;
Exo-2-methyl-6-(3-butylthio-1,2,5-thiadiazol-4-yl)-1-azabicyclo[3.2.1]octane;
Exo-8-methyl-6-(3-butylthio-1,2,5-thiadiazol-4-yl)-1-azabicyclo[3.2.1]octane;
Exo-2-methyl-6-(3-hexylthio-1,2,5-thiadiazol-4-yl)-1-azabicyclo[3.2.1]octane;
Exo-8-methyl-6-(3-hexylthio-1,2,5-thiadiazol-4-yl)-1-azabicyclo[3.2.1]octane;
or a pharmaceutically acceptable salt thereof.

34. The compound according to claim 1 which is:
(−)-Endo-6-(3-propylthio-1,2,5-thiadiazol-4-yl)-1-azabicyclo[3.2.1]octane;
(+)-Exo-(5R,6R)-6-(3-isohexylthio-1,2,5-thiadiazol-4-yl)-1-azabicyclo[3.2.1]octane;
(−)-Exo-6-(3-isohexylthio-1,2,5-thiadiazol-4-yl)-1-azabicyclo[3.2.1]octane;
(+)-Endo-6-(3-isohexylthio-1,2,5-thiadiazol-4-yl)-1-azabicyclo[3.2.1]octane;
(+)-Endo-6-(3-propylthio-1,2,5-thiadiazol-4-yl)-1-azabicyclo[3.2.1]octane;
(+)-Exo-6-(3-methylthio-1,2,5-thiadiazol-4-yl)-1-azabicyclo[3.2.1]octane;
(+)-Exo-6-(3-ethylthio-1,2,5-thiadiazol-4-yl)-1-azabicyclo[3.2.1]octane;
(+)-Exo-6-(3-pentylthio-1,2,5-thiadiazol-4-yl)-1-azabicyclo[3.2.1]octane;
(+)-Exo-6-(3-hexylthio-1,2,5-thiadiazol-4-yl)-1-azabicyclo[3.2.1]octane;
(−)-Exo-6-(3-methylthio-1,2,5-thiadiazol-4-yl)-1-azabicyclo[3.2.1]octane;
(−)-Exo-6-(3-ethylthio-1,2,5-thiadiazol-4-yl)-1-azabicyclo[3.2.1]octane;
(−)-Exo-6-(3-pentylthio-1,2,5-thiadiazol-4-yl)-1-azabicyclo[3.2.1]octane;
(−)-Exo-6-(3-hexylthio-1,2,5-thiadiazol-4-yl)-1-azabicyclo[3.2.1]octane;
(+)-Endo-6-(3-methylthio-1,2,5-thiadiazol-4-yl)-1-azabicyclo[3.2.1]octane;
(+)-Endo-6-(3-ethylthio-1,2,5-thiadiazol-4-yl)-1-azabicyclo[3.2.1]octane;
(+)-Endo-6-(3-pentylthio-1,2,5-thiadiazol-4-yl)-1-azabicyclo[3.2.1]octane;
(+)-Endo-6-(3-hexylthio-1,2,5-thiadiazol-4-yl)-1-azabicyclo[3.2.1]octane;
(−)-Endo-6-(3-methylthio-1,2,5-thiadiazol-4-yl)-1-azabicyclo[3.2.1]octane;
(−)-Endo-6-(3-ethylthio-1,2,5-thiadiazol-4-yl)-1-azabicyclo[3.2.1]octane;
(−)-Endo-6-(3-pentylthio-1,2,5-thiadiazol-4-yl)-1-azabicyclo[3.2.1]octane;
(−)-Endo-6-(3-hexylthio-1,2,5-thiadiazol-4-yl)-1-azabicyclo[3.2.1]octane; or
a pharmaceutically acceptable salt thereof.

35. The compound according to claim 1 which is:
Exo-2-methyl-6-(3-chloro-1,2,5-thiadiazol-4-yl)-1-azabicyclo[3.2.1]octane;
Endo-2-methyl-6-(3-chloro-1,2,5-thiadiazol-4-yl)-1-azabicyclo[3.2.1]octane;
Exo-8-methyl-6-(3-chloro-1,2,5-thiadiazol-4-yl)-1-azabicyclo[3.2.1]octane;
Endo-8-methyl-6-(3-chloro-1,2,5-thiadiazol-4-yl)-1-azabicyclo[3.2.1]octane; or
a pharmaceutically acceptable salt thereof.

36. The compound according to claim 1 which is:
Exo-6-(3-(2-methoxyethylthio)-1,2,5-thiadiazol-4-yl)-1-azabicyclo[3.2.1]octane;
Exo-6-(3-(3-hydroxypropylthio)-1,2,5-thiadiazol-4-yl)-1-azabicyclo[3.2.1]octane;
Endo-6-(3-(2-methoxyethylthio)-1,2,5-thiadiazol-4-yl)-1-azabicyclo[3.2.1]octane;
(+)-Exo-6-(3-(2-hydroxyethylthio)-1,2,5-thiadiazol-4-yl)-1-azabicyclo[3.2.1]octane; or
a pharmaceutically acceptable salt thereof.

37. The compound according to claim 1 which is:
(+)-Exo-(5R,6R)-6-(3-propylsulfonyl-1,2,5-thiadiazol-4-yl)-1-azabicyclo[3.2.1]octane;
(−)-Exo-(5S,6S)-6-(3-propylsulfonyl-1,2,5-thiadiazol-4-yl)-1-azabicyclo[3.2.1]octane;
(+)-Exo-6-(3-(3-(2-thienyl)propylthio)-1,2,5-thiadiazol-4-yl)-1-azabicyclo[3.2.1]octane;
Exo-6-(3-cyclopropylmethylthio-1,2,5-thiadiazol-4-yl)-1-azabicyclo[3.2.1]octane;
Exo-6-(3-(2-(1,3-dioxolane-2-yl)-ethylthio)-1,2,5-thiadiazol-4-yl)-1-azabicyclo[3.2.1]octane;
Endo-6-(3-cyclopropylmethylthio-1,2,5-thiadiazol-4-yl)-1-azabicyclo[3.2.1]octane;
Exo-6-(3-propylsulfonyl-1,2,5-thiadiazol-4-yl)-1-azabicyclo[3.2.1]octane; or
a pharmaceutically acceptable salt thereof.

38. A pharmaceutical composition comprising an effective amount of a compound according to claim 1 together with a pharmaceutically acceptable carrier or diluent.

39. The pharmaceutical composition according to claim 38 in the form of an oral dosage unit or a parenteral dosage unit.

40. The pharmaceutical composition according to claim 39, wherein said dosage unit comprises from about 1 to about 100 mg of the compound.

41. A method of stimulating the cognitive functions of the forebrain and hippocampus comprising administering to a subject in need thereof an effective amount of a compound according to claim 1.

42. A method of treating Alzheimer's disease comprising administering to a subject in need thereof an effective amount of a compound according to claim 1.

43. A method of treating glaucoma comprising administering to a subject in need thereof an effective amount of a compound according to claim 1.

44. A method of providing an analgesic effect comprising administering to a subject in need thereof an effective amount of a compound according to claim 1.

45. A method of stimulating the cognitive functions of the forebrain and hippocampus comprising administering to a subject in need thereof an effective amount of a pharmaceutical composition according to claim 38.

46. A method of treating Alzheimer's disease comprising administering to a subject in need thereof an effective amount of a pharmaceutical composition according to claim 38.

47. A method of treating glaucoma comprising administering to a subject in need thereof an effective amount of a pharmaceutical composition according to claim 38.

48. A method of providing an analgesic effect comprising administering to a subject in need thereof an effective amount of a pharmaceutical composition according to claim 38.

49. A pharmaceutical composition comprising an effective amount of a compound according to claim 10 together with a pharmaceutically acceptable carrier or diluent.

50. A method of stimulating the cognitive functions of the forebrain and hippocampus comprising administering to a subject in need thereof an effective amount of a compound according to claim 10.

51. A method of treating Alzheimer's disease comprising administering to a subject in need thereof an effective amount of a compound according to claim 10.

52. A method of treating glaucoma comprising administering to a subject in need thereof an effective amount of a compound according to claim 10.

53. A method of providing an analgesic effect comprising administering to a subject in need thereof an effective amount of a compound according to claim 10.

54. A method of stimulating the cognitive functions of the forebrain and hippocampus comprising administering to a subject in need thereof an effective amount of a pharmaceutical composition according to claim 49.

55. A method of treating Alzheimer's disease comprising administering to a subject in need thereof an effective amount of a pharmaceutical composition according to claim 49.

56. A method of treating glaucoma comprising administering to a subject in need thereof an effective mount of a pharmaceutical composition according to claim 49.

57. A method of providing an analgesic effect comprising administering to a subject in need thereof an effective amount of a pharmaceutical composition according to claim 49.

58. A pharmaceutical composition comprising an effective amount of a compound according to claim 2 together with a pharmaceutically acceptable carrier or diluent.

59. A method of stimulating the cognitive functions of the forebrain and hippocampus comprising administering to a subject in need thereof an effective amount of a compound according to claim 2.

60. A method of treating Alzheimer's disease comprising administering to a subject in need thereof an effective amount of a compound according to claim 2.

61. A method of treating glaucoma comprising administering to a subject in need thereof an effective amount of a compound according to claim 2.

62. A method of providing an analgesic effect comprising administering to a subject in need thereof an effective amount of a compound according to claim 2.

63. A method of stimulating the cognitive functions of the forebrain and hippocampus comprising administering to a subject in need thereof an effective amount of a pharmaceutical composition according to claim 58.

64. A method of treating Alzheimer's disease comprising administering to a subject in need thereof an effective mount of a pharmaceutical composition according to claim 58.

65. A method of treating glaucoma comprising administering to a subject in need thereof an effective amount of a pharmaceutical composition according to claim 58.

66. A method of providing an analgesic effect comprising administering to a subject in need thereof an effective amount of a pharmaceutical composition according to claim 58.

67. The compound according to claim 1, wherein R is $C_{3-7}$-cycloalkyl, $C_{4-8}$-(cycloalkylalkyl), —Z—$C_{3-7}$-cycloalkyl or —Z—$C_{4-8}$-(cycloalkylalkyl).

* * * * *